(12) United States Patent
Nagata et al.

(10) Patent No.: US 7,128,905 B2
(45) Date of Patent: Oct. 31, 2006

(54) METHOD OF TREATING GRAFT VERSUS HOST DISEASE BY ADMINISTRATION OF A FAS ANTAGONIST

(75) Inventors: Shigekazu Nagata, Osaka (JP); Takehiro Yatomi, Tokyo (JP); Takashi Suda, Osaka (JP)

(73) Assignees: Mochida Pharmaceutical Co., Ltd., Tokyo (JP); Osaka Bioscience Institute, Osaka (JP)

( * ) Notice: Subject to any disclaimer, the term of this patent is extended or adjusted under 35 U.S.C. 154(b) by 578 days.

(21) Appl. No.: 10/084,139

(22) Filed: Feb. 28, 2002

(65) Prior Publication Data

US 2003/0109416 A1 Jun. 12, 2003

Related U.S. Application Data

(62) Division of application No. 09/297,328, filed as application No. PCT/JP97/03978 on Oct. 31, 1997, now abandoned.

(30) Foreign Application Priority Data

| Oct. 31, 1996 | (JP) | ................... 8-290459 |
| Dec. 27, 1996 | (JP) | ................... 8-351718 |
| Sep. 26, 1997 | (JP) | ................... 9-262521 |

(51) Int. Cl.
*A61K 39/395* (2006.01)
*A61K 39/00* (2006.01)
*A61K 38/00* (2006.01)

(52) U.S. Cl. ............... 424/130.1; 424/133.1; 424/141.1; 424/158.1; 424/184.1; 424/192.1; 530/387.1; 530/387.3; 530/388.23; 530/350; 514/2; 514/12

(58) Field of Classification Search ................ 530/350, 530/351; 514/1
See application file for complete search history.

(56) References Cited

U.S. PATENT DOCUMENTS

| 5,620,889 A | * | 4/1997 | Lynch et al. ............... 435/332 |
| 5,652,210 A | * | 7/1997 | Barr et al. ................. 514/2 |
| 5,759,536 A | * | 6/1998 | Bellgrau et al. ............ 424/93.21 |
| 5,776,718 A | * | 7/1998 | Palmer et al. .............. 435/23 |
| 5,801,154 A | * | 9/1998 | Baracchini et al. ......... 435/325 |
| 6,007,995 A | * | 12/1999 | Baker et al. ............... 435/325 |

FOREIGN PATENT DOCUMENTS

| JP | 8208515 | 8/1996 |
| JP | 9110722 | 4/1997 |
| JP | 9124509 | 5/1997 |
| WO | WO 9510540 | 4/1995 |
| WO | WO 9518819 | 7/1995 |
| WO | WO 9640041 | 12/1996 |
| WO | WO 9712632 | 4/1997 |
| WO | WO 9733617 | 9/1997 |

OTHER PUBLICATIONS

Science News Report, Science 269, p. 1050, col. 2, paragraph 1, lines 6-15.*
Anderson, Scientific American, Sep. 1995, pp. 124-128.*
Blau et al., (The New England Journal of Medicine, Nov. 2, 1995, pp. 1204-1207.*
Barun et al., J. Exp. Med., vol. 183, pp. 657-661, Feb. 1996.*
by Du et al., BBRC, vol. 226, pp. 595-600, Sep. 24, 1996.*
Agrawal et al., TIBTECH 1996, 14:376-387.*
Braasch, D. A. Biochemistry. Apr. 2002; 41(14):4503-4510.*
Branch, A. D.,Trends Biochem Sci. Feb. 1998;23(2):45-50.*
Gewirtz et al., Proc. Natl. Acad. Sci. 1996. v 93, pp. 3161-3163.*
Tamm, I. et al. The Lancet. Aug. 2001, 358:489-497.*
Gabler et al., Nucleic Acids Research. 2003, vol. 31, No. 15, pp. e79.*
Baker et al., The Journal of Experimental Medicine. vol. 183, Jun. 1996, pp. 2645-2656.*
Agrawal, S. Trends Biotechnol. Oct. 1996; 14(10):376-87.*
Gewirtz et al., Proc. Natl. Acad. Sci. v 93, pp. 3161-3163.*
Braasch, D. A. Biochemistry. Apr. 2002; 41(14): 4503-4510.*
Branch, A. D., (1998). Trends Biochem Sci. Feb. 1998;23(2):45-59.*
Galle et al., J. Exp. Med., vol. 182, No. 5 (1995) pp. 1223-1230.
M. Tanaka et al., *Nature Medicine*, vol. 2, No. 3, Mar. 1996, pp. 317-322.
Derwent Publications Ltd., XP-002124972, Nov. 7, 1995.
M. Enari et al., *Nature*, vol. 375, No. 6526, May 1995, pp. 78-81.
T. Knodo et al., *Nature Medicine*, vol. 3, No. 4, Apr. 1997, pp. 409-713.

* cited by examiner

*Primary Examiner*—Eileen B. O'Hara
(74) *Attorney, Agent, or Firm*—Birch, Stewart, Kolasch & Birch, LLP

(57) ABSTRACT

The present invention is drawn to methods of preventing and treating diseases wherein the involvement of apoptosis has been indicated.

3 Claims, 21 Drawing Sheets

FIG. 1

```
ATG ATG TCC TCT GCT CAG TTC CTT GGT CTC CTG TTG CTC TGT TTT CAA GGT ACC AGA TGT   60
 M   M   S   S   A   Q   F   L   G   L   L   L   L   C   F   Q   G   T   R   C

GAT ATC CAG ATG ACA CAG ACT ACA TCC CTG TCT GCC TCT CTG GGA GAC AGA GTC ACC       120
 D   I   Q   M   T   Q   T   T   S   L   S   A   S   L   G   D   R   V   T
 =   =

ATC AGT TGC AGG GCC AGT CAG GAC ATT AGC AAT TAT TTA AAC TGG TAT CAG CAG AAA CCA   180
 I   S   C   R   A   S   Q   D   I   S   N   Y   L   N   W   Y   Q   Q   K   P
         ─── ─── ─── ─── ─── ─── ─── ─── ─── ───

GAT GGA ACT GTT AAA CTC CTG ATC TAC TAC ACA TCA AGA TTA CAC TCA GGA GTC CCA TCA   240
 D   G   T   V   K   L   L   I   Y   Y   T   S   R   L   H   S   G   V   P   S
                                 ─── ─── ─── ─── ─── ───

AGG TTC AGT GGC AGT GGG TCT GGG ACA GAT TAT TCT CTC ACC ATT AGC AAC CTG GAA CAA   300
 R   F   S   G   S   G   S   G   T   D   Y   S   L   T   I   S   N   L   E   Q

GGA GAT ATT GCC ACT TAC TTT TGC CAA CAG GGT AGT ACG CTT CCG TGG ACG TTC GGT GGA   360
 G   D   I   A   T   Y   F   C   Q   Q   G   S   T   L   P   W   T   F   G   G
                                 ─── ─── ─── ─── ─── ─── ───

GGC ACC AAG CTG GAA ATC AAA
 G   T   K   L   E   I   K
```

FIG. 2

ATG GAT TGG GTG TGG ACC TTG CTA TTC CTG ATA GCA GCT GCC CAA AGT GCC CAA GCA CAG
M   D   W   V   W   T   L   L   F   L   I   A   A   A   Q   S   A   Q   A   Q
                                                                                30                                60

ATC CAG TTG GTG CAG TCT GGA CCT GAG CTG AAG AAG CCT GGA GAG ACA GTC AAG ATC TCC
I   Q   L   V   Q   S   G   P   E   L   K   K   P   G   E   T   V   K   I   S
                                                                                90                               120

TGC AAG GCT TCT GGG TAT ACC TTC ACA GAA TAT CCA ATG CAC TGG GTG AAG CAG GCT CCA
C   K   A   S   G   Y   T   F   T   E   Y   P   M   H   W   V   K   Q   A   P
                                                                               150                               180

GGA AAG GGT TTC AAG TGG ATG GGC ATG ATA TAC ACC GAC ACT GGA GAG CCA TCA TAT GCT
G   K   G   F   K   W   M   G   M   I   Y   T   D   T   G   E   P   S   Y   A
                                                                               210                               240

GAA GAG TTC AAG GGG CGG TTT GCC TTC TCT TTG GAG ACC TCT GCC AGC ACT GCC TAT TTG
E   E   F   K   G   R   F   A   F   S   L   E   T   S   A   S   T   A   Y   L
                                                                               270                               300

CAG ATC AAC TTC CTC AAA AAT GAG GAC ACG GCT ACA TAT TTC TGT GTA AGA TTT TAC TGG
Q   I   N   F   L   K   N   E   D   T   A   T   Y   F   C   V   R   F   Y   W
                                                                               330                               360

GAT TAC TTT GAC TAC TGG GGC CAA GGC ACC ACT CTC ACA GTC TCC TCA
D   Y   F   D   Y   W   G   Q   G   T   T   L   T   V   S   S
                                                                390

FIG. 3

ATG GAG ACC GAT ACC CTC CTG CTA TGG GTC CTC CTG CTA TGG GTC CCA GGA TCA ACC GGA 60
 M   E   T   D   T   L   L   L   W   V   L   L   L   W   V   P   G   S   T   G

GAT ATT CAG ATG ACC CAG AGT CCG TCG ACC CTC TCT GCT AGC GTC GGG GAT AGG GTC ACC 120
 D   I   Q   M   T   Q   S   P   S   T   L   S   A   S   V   G   D   R   V   T

ATA ACT TGC AGG GCA AGT CAG GAC ATT TCG AAT TAT TTA AAC TGG TAT CAG CAG AAG CCA 180
 I   T   C   R   A   S   Q   D   I   S   N   Y   L   N   W   Y   Q   Q   K   P

GGC AAA GCT CCC AAG CTT CTA ATT TAT TAC ACA TCA AGA TTA CAC TCA GGG GTA CCT TCA 240
 G   K   A   P   K   L   L   I   Y   Y   T   S   R   L   H   S   G   V   P   S

CGC TTC AGT GGC AGT GGA TCT GGG ACC AAT TAT ACC CTC ACA ATC TCG AGT CTG CAG CCA 300
 R   F   S   G   S   G   S   G   T   N   Y   T   L   T   I   S   S   L   Q   P

GAT GAT TTC GCC ACT TAT TTT TGC CAA CAG GGT AGT ACG CTT CCG TGG ACG TTC GGT CAG 360
 D   D   F   A   T   Y   F   C   Q   Q   G   S   T   L   P   W   T   F   G   Q

GGG ACC AAG GTG GAG GTC AAA
 G   T   K   V   E   V   K

FIG. 4

ATG GAT TGG GTG TGG ACC TTG CTA TTC CTG ATA GCT GCA GCC CAA AGT GCC CAA GCA CAG 60
 M   D   W   V   W   T   L   L   F   L   I   A   A   A   Q   S   A   Q   A   Q

GTC CAG TTG GTG CAG TCT GGA GCT GAG GTG AAG AAG CCT GGA AGC TCA GTG AAG GTG TCC 120
 V   Q   L   V   Q   S   G   A   E   V   K   K   P   G   S   S   V   K   V   S

TGC AAA GCT TCT GGG TAT ACC TTC ACA GAA TAT CCA ATG CAC TGG GTG AGA CAG GCT CCA 180
 C   K   A   S   G   Y   T   F   T   E   Y   P   M   H   W   V   R   Q   A   P

GGA CAG GGT TTC AAG TGG ATG GGC ATA TAC ACC GAC ACT GGA GAG CCA TCA TAT GCT 240
 G   Q   G   F   K   W   M   G   M   I   Y   T   D   T   G   E   P   S   Y   A

GAA GAG TTC AAG GGA CGG TTT ACA TTC ACT TTG GAC ACC TCT ACC AAC ACT GCC TAT ATG 300
 E   E   F   K   G   R   F   T   F   T   L   D   T   S   T   N   T   A   Y   M

GAG CTC AGC TCT CTC AGG TCT GAG GAC ACG GCT GTC TAT TAC TGT GTA AGA TTT TAC TGG 360
 E   L   S   S   L   R   S   E   D   T   A   V   Y   Y   C   V   R   F   Y   W

GAT TAC TTT GAC TAC TGG GGT CAA GGT ACC CTG GTC ACA GTC TCC TCA
 D   Y   F   D   Y   W   G   Q   G   T   L   V   T   V   S   S

FIG. 5 tttcttccatttcaggtgtcgtgaggaattcacc

50

| ATG | CTG | GGC | ATC | TGG | ACC | CTC | CTA | CCT | CTG |
|-----|-----|-----|-----|-----|-----|-----|-----|-----|-----|
| Met | Leu | Gly | Ile | Trp | Thr | Leu | Leu | Pro | Leu |

−10 hFas antigen signal peptide

| GTT | CTG | ACT | AGT | GTC | GCT | ACT | CAG | AAC | TTG |
|-----|-----|-----|-----|-----|-----|-----|-----|-----|-----|
| Val | Leu | Thr | Ser | Val | Ala | Thr | Gln | Asn | Leu |

−1  1

100                    →hFas(nd29)

GAA GGC CTG CAT CAT GAT GGC CAA TTC TGC
Glu Gly Leu His His Asp Gly Gln Phe Cys

150

CAT AAG CCC TGT CCT CCA GGT GAA AGG AAA
His Lys Pro Cys Pro Pro Gly Glu Arg Lys

GCT AGG GAC TGC ACA GTC AAT GGG GAT GAA
Ala Arg Asp Cys Thr Val Asn Gly Asp Glu

200

CCA GAC TGC GTG CCC TGC CAA GAA GGG AAG
Pro Asp Cys Val Pro Cys Gln Glu Gly Lys

GAG TAC ACA GAC AAA GCC CAT TTT TCT TCC
Glu Tyr Thr Asp Lys Ala His Phe Ser Ser

50

250

AAA TGC AGA AGA TGT AGA TTG TGT GAT GAA
Lys Cys Arg Arg Cys Arg Leu Cys Asp Glu

FIG. 6

```
                                      300
GGA CAT GGC TTA GAA GTG GAA ATA AAC TGC
Gly His Gly Leu Glu Val Glu Ile Asn Cys
                                    *

ACC CGG ACC CAG AAT ACC AAG TGC AGA TGT
Thr Arg Thr Gln Asn Thr Lys Cys Arg Cys

350
AAA CCA AAC TTT TTT TGT AAC TCT ACT GTA
Lys Pro Asn Phe Phe Cys Asn Ser Thr Val
                        *

TGT GAA CAC TGT GAC CCT TGC ACC AAA TGT
Cys Glu His Cys Asp Pro Cys Thr Lys Cys
                        100
    400
GAA CAT GGA ATC ATC AAG GAA TGC ACA CTC
Glu His Gly Ile Ile Lys Glu Cys Thr Leu

450
ACC AGC AAC ACC AAG TGC AAA GAG GAA GGA
Thr Ser Asn Thr Lys Cys Lys Glu Glu Gly

TCC AGA TCT AAC GAG CCC AAA TCT TGT GAC
Ser Arg Ser Asn Glu Pro Lys Ser Cys Asp
                     └─→ hIgG1 Fc
                     500
AAA ACT CAC ACA TGC CCA CCG TGC CCA GCA
Lys Thr His Thr Cys Pro Pro Cys Pro Ala
```

FIG. 7

```
CCT GAA CTC CTG GGG GGA CCG TCA GTC TTC
Pro Glu Leu Leu Gly Gly Pro Ser Val Phe
                    150
    550
CTC TTC CCC CCA AAA CCC AAG GAC ACC CTC
Leu Phe Pro Pro Lys Pro Lys Asp Thr Leu

600
ATG ATC TCC CGG ACC CCT GAG GTC ACA TGC
Met Ile Ser Arg Thr Pro Glu Val Thr Cys

GTG GTG GTG GAC GTG AGC CAC GAA GAC CCT
Val Val Val Asp Val Ser His Glu Asp Pro
                650
GAG GTC AAG TTC AAC TGG TAC GTG GAC GGC
Glu Val Lys Phe Asn Trp Tyr Val Asp Gly

GTG GAG GTG CAT AAT GCC AAG ACA AAG CCG
Val Glu Val His Asn Ala Lys Thr Lys Pro
                            200
    700
CGG GAG GAG CAG TAC AAC AGC ACG TAC CGT
Arg Glu Glu Gln Tyr Asn Ser Thr Tyr Arg
                        *
                                750
GTG GTC AGC GTC CTC ACC GTC CTG CAC CAG
Val Val Ser Val Leu Thr Val Leu His Gln
```

FIG. 8

```
GAC TGG CTG AAT GGC AAG GAG TAC AAG TGC
Asp Trp Leu Asn Gly Lys Glu Tyr Lys Cys
                    800
AAG GTC TCC AAC AAA GCC CTC CCA GCC CCC
Lys Val Ser Asn Lys Ala Leu Pro Ala Pro

ATC GAG AAA ACC ATC TCC AAA GCC AAA GGG
Ile Glu Lys Thr Ile Ser Lys Ala Lys Gly
                        250
    850
CAG CCC CGA GAA CCA CAG GTG TAC ACC CTG
Gln Pro Arg Glu Pro Gln Val Tyr Thr Leu
                                    900
CCC CCA TCC CGG GAT GAG CTG ACC AAG AAC
Pro Pro Ser Arg Asp Glu Leu Thr Lys Asn

CAG GTC AGC CTG ACC TGC CTG GTC AAA GGC
Gln Val Ser Leu Thr Cys Leu Val Lys Gly
                950
TTC TAT CCC AGC GAC ATC GCC GTG GAG TGG
Phe Tyr Pro Ser Asp Ile Ala Val Glu Trp

GAG AGC AAT GGG CAG CCG GAG AAC AAC TAC
Glu Ser Asn Gly Gln Pro Glu Asn Asn Tyr
                        300
```

FIG. 9

```
     1000
AAG ACC ACG CCT CCC GTG CTG GAC TCC GAC
Lys Thr Thr Pro Pro Val Leu Asp Ser Asp

1050
GGC TCC TTC TTC CTC TAC AGC AAG CTC ACC
Gly Ser Phe Phe Leu Tyr Ser Lys Leu Thr

GTG GAC AAG AGC AGG TGG CAG CAG GGG AAC
Val Asp Lys Ser Arg Trp Gln Gln Gly Asn

1100
GTC TTC TCA TGC TCC GTG ATG CAT GAG GCT
Val Phe Ser Cys Ser Val Met His Glu Ala

CTG CAC AAC CAC TAC ACG CAG AAG AGC CTC
Leu His Asn His Tyr Thr Gln Lys Ser Leu
                          350
    1150
TCC CTG TCT CCG GGT AAA TGA TAG  ggtacc
Ser Leu Ser Pro Gly Lys * * ttctgag
```

FIG. 10 tttcttccatttcaggtgtcgtgaggaattcacc

50

| ATG | CTG | GGC | ATC | TGG | ACC | CTC | CTA | CCT | CTG |
|-----|-----|-----|-----|-----|-----|-----|-----|-----|-----|
| Met | Leu | Gly | Ile | Trp | Thr | Leu | Leu | Pro | Leu |

−10 hFas antigen signal peptide

| GTT | CTG | ACT | AGT | GTC | GCT | ACT | CAG | AAC | TTG |
|-----|-----|-----|-----|-----|-----|-----|-----|-----|-----|
| Val | Leu | Thr | Ser | Val | Ala | Thr | Gln | Asn | Leu |

−1 | 1
→ hFas(nd29)

100

| GAA | GGC | CTG | CAT | CAT | GAT | GGC | CAA | TTC | TGC |
|-----|-----|-----|-----|-----|-----|-----|-----|-----|-----|
| Glu | Gly | Leu | His | His | Asp | Gly | Gln | Phe | Cys |

150

| CAT | AAG | CCC | TGT | CCT | CCA | GGT | GAA | AGG | AAA |
|-----|-----|-----|-----|-----|-----|-----|-----|-----|-----|
| His | Lys | Pro | Cys | Pro | Pro | Gly | Glu | Arg | Lys |

| GCT | AGG | GAC | TGC | ACA | GTC | AAT | GGG | GAT | GAA |
|-----|-----|-----|-----|-----|-----|-----|-----|-----|-----|
| Ala | Arg | Asp | Cys | Thr | Val | Asn | Gly | Asp | Glu |

200

| CCA | GAC | TGC | GTG | CCC | TGC | CAA | GAA | GGG | AAG |
|-----|-----|-----|-----|-----|-----|-----|-----|-----|-----|
| Pro | Asp | Cys | Val | Pro | Cys | Gln | Glu | Gly | Lys |

| GAG | TAC | ACA | GAC | AAA | GCC | CAT | TTT | TCT | TCC |
|-----|-----|-----|-----|-----|-----|-----|-----|-----|-----|
| Glu | Tyr | Thr | Asp | Lys | Ala | His | Phe | Ser | Ser |

50

250

| AAA | TGC | AGA | AGA | TGT | AGA | TTG | TGT | GAT | GAA |
|-----|-----|-----|-----|-----|-----|-----|-----|-----|-----|
| Lys | Cys | Arg | Arg | Cys | Arg | Leu | Cys | Asp | Glu |

FIG. 11

```
                                            300
GGA CAT GGC TTA GAA GTG GAA ATA AAC TGC
Gly His Gly Leu Glu Val Glu Ile Asn Cys
                                        *

ACC CGG ACC CAG AAT ACC AAG TGC AGA TGT
Thr Arg Thr Gln Asn Thr Lys Cys Arg Cys

350
AAA CCA AAC TTT TTT TGT AAC TCT ACT GTA
Lys Pro Asn Phe Phe Cys Asn Ser Thr Val
                        *

TGT GAA CAC TGT GAC CCT TGC ACC AAA TGT
Cys Glu His Cys Asp Pro Cys Thr Lys Cys
                            100
    400
GAA CAT GGA ATC ATC AAG GAA TGC ACA CTC
Glu His Gly Ile Ile Lys Glu Cys Thr Leu

450
ACC AGC AAC ACC AAG TGC AAA GAG GAA GGA
Thr Ser Asn Thr Lys Cys Lys Glu Glu Gly

TCC AGA TCT AAC GAG CCC AAA TCT TGT GAC
Ser Arg Ser Asn Glu Pro Lys Ser Cys Asp
                     └──→ hIgG1 hinge
              500
AAA ACT CAC ACA TGC CCA CCG TGC CCA TAG
Lys Thr His Thr Cys Pro Pro Cys Pro ***
```

FIG. 12

TGA  ggtacccttctgag

SEQUENCE LISTING

<160> NUMBER OF SEQ ID NOS: 12

<210> SEQ ID NO 1
<211> LENGTH: 381
<212> TYPE: DNA
<213> ORGANISM: Mus sp.
<220> FEATURE:
<221> NAME/KEY: CDS
<222> LOCATION: (1)..(381)

<400> SEQUENCE: 1

```
atg atg tcc tct gct cag ttc ctt ggt ctc ctg ttg ctc tgt ttt caa      48
Met Met Ser Ser Ala Gln Phe Leu Gly Leu Leu Leu Leu Cys Phe Gln
  1               5                  10                  15 ggt acc aga tgt gat atc cag atg aca cag act aca tcc tcc ctg tct      96
Gly Thr Arg Cys Asp Ile Gln Met Thr Gln Thr Thr Ser Ser Leu Ser
             20                  25                  30 gcc tct ctg gga gac aga gtc acc atc agt tgc agg gcc agt cag gac     144
Ala Ser Leu Gly Asp Arg Val Thr Ile Ser Cys Arg Ala Ser Gln Asp
         35                  40                  45 att agc aat tat tta aac tgg tat cag cag aaa cca gat gga act gtt     192
Ile Ser Asn Tyr Leu Asn Trp Tyr Gln Gln Lys Pro Asp Gly Thr Val
     50                  55                  60 aaa ctc ctg atc tac tac aca tca aga tta cac tca gga gtc cca tca     240
Lys Leu Leu Ile Tyr Tyr Thr Ser Arg Leu His Ser Gly Val Pro Ser
 65                  70                  75                  80 agg ttc agt ggc agt ggg tct ggg aca aat tat tct ctc acc att agc     288
Arg Phe Ser Gly Ser Gly Ser Gly Thr Asn Tyr Ser Leu Thr Ile Ser
                 85                  90                  95 aac ctg gaa caa gga gat att gcc act tac ttt tgc caa cag ggt agt     336
Asn Leu Glu Gln Gly Asp Ile Ala Thr Tyr Phe Cys Gln Gln Gly Ser
            100                 105                 110 acg ctt ccg tgg acg ttc ggt gga ggc acc aag ctg gaa atc aaa         381
Thr Leu Pro Trp Thr Phe Gly Gly Gly Thr Lys Leu Glu Ile Lys
        115                 120                 125
```

<210> SEQ ID NO 2
<211> LENGTH: 127
<212> TYPE: PRT
<213> ORGANISM: Mus sp.

<400> SEQUENCE: 2

```
Met Met Ser Ser Ala Gln Phe Leu Gly Leu Leu Leu Leu Cys Phe Gln
  1               5                  10                  15

Gly Thr Arg Cys Asp Ile Gln Met Thr Gln Thr Thr Ser Ser Leu Ser
             20                  25                  30
```

-continued

Ala Ser Leu Gly Asp Arg Val Thr Ile Ser Cys Arg Ala Ser Gln Asp
                35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asn Tyr Ser Leu Thr Ile Ser
                85                  90                  95

Asn Leu Glu Gln Gly Asp Ile Ala Thr Tyr Phe Cys Gln Gln Gly Ser
            100                 105                 110

Thr Leu Pro Trp Thr Phe Gly Gly Gly Thr Lys Leu Glu Ile Lys
        115                 120                 125

<210> SEQ ID NO 3
<211> LENGTH: 408
<212> TYPE: DNA
<213> ORGANISM: Mus sp.
<220> FEATURE:
<221> NAME/KEY: CDS
<222> LOCATION: (1)..(408)

<400> SEQUENCE: 3 atg gat tgg gtg tgg acc ttg cta ttc ctg ata gca gct gcc caa agt      48
Met Asp Trp Val Trp Thr Leu Leu Phe Leu Ile Ala Ala Ala Gln Ser
 1               5                   10                  15 gcc caa gca cag atc cag ttg gtg cag tct gga cct gag ctg aag aag      96
Ala Gln Ala Gln Ile Gln Leu Val Gln Ser Gly Pro Glu Leu Lys Lys
            20                  25                  30 cct gga gag aca gtc aag atc tcc tgc aag gct tct ggg tat acc ttc     144
Pro Gly Glu Thr Val Lys Ile Ser Cys Lys Ala Ser Gly Tyr Thr Phe
        35                  40                  45 aca gaa tat cca atg cac tgg gtg aag cag gct cca gga aag ggt ttc     192
Thr Glu Tyr Pro Met His Trp Val Lys Gln Ala Pro Gly Lys Gly Phe
    50                  55                  60 aag tgg atg ggc atg ata tac acc gac act gga gag cca tca tat gct     240
Lys Trp Met Gly Met Ile Tyr Thr Asp Thr Gly Glu Pro Ser Tyr Ala
65                  70                  75                  80 gaa gag ttc aag ggg cgg ttt gcc ttc tct ttg gag acc tct gcc agc     288
Glu Glu Phe Lys Gly Arg Phe Ala Phe Ser Leu Glu Thr Ser Ala Ser
                85                  90                  95 act gcc tat ttg cag atc aac ttc ctc aaa aat gag gac acg gct aca     336
Thr Ala Tyr Leu Gln Ile Asn Phe Leu Lys Asn Glu Asp Thr Ala Thr
            100                 105                 110 tat ttc tgt gta aga ttt tac tgg gat tac ttt gac tac tgg ggc caa     384
Tyr Phe Cys Val Arg Phe Tyr Trp Asp Tyr Phe Asp Tyr Trp Gly Gln
        115                 120                 125 ggc acc act ctc aca gtc tcc tca                                     408
Gly Thr Thr Leu Thr Val Ser Ser
    130                 135

<210> SEQ ID NO 4
<211> LENGTH: 136
<212> TYPE: PRT
<213> ORGANISM: Mus sp.

<400> SEQUENCE: 4

Met Asp Trp Val Trp Thr Leu Leu Phe Leu Ile Ala Ala Ala Gln Ser
 1               5                   10                  15

Ala Gln Ala Gln Ile Gln Leu Val Gln Ser Gly Pro Glu Leu Lys Lys
            20                  25                  30

```
            Pro Gly Glu Thr Val Lys Ile Ser Cys Lys Ala Ser Gly Tyr Thr Phe
                         35                  40                  45

Thr Glu Tyr Pro Met His Trp Val Lys Gln Ala Pro Gly Lys Gly Phe
             50                  55                  60

Lys Trp Met Gly Met Ile Tyr Thr Asp Thr Gly Glu Pro Ser Tyr Ala
             65                  70                  75                  80

Glu Glu Phe Lys Gly Arg Phe Ala Phe Ser Leu Glu Thr Ser Ala Ser
                             85                  90                  95

Thr Ala Tyr Leu Gln Ile Asn Phe Leu Lys Asn Glu Asp Thr Ala Thr
                        100                 105                 110

Tyr Phe Cys Val Arg Phe Tyr Trp Asp Tyr Phe Asp Tyr Trp Gly Gln
                    115                 120                 125

Gly Thr Thr Leu Thr Val Ser Ser
                130                 135

<210> SEQ ID NO 5
<211> LENGTH: 381
<212> TYPE: DNA
<213> ORGANISM: Homo sapiens
<220> FEATURE:
<221> NAME/KEY: CDS
<222> LOCATION: (1)..(381)

<400> SEQUENCE: 5 atg gag acc gat acc ctc ctg cta tgg gtc ctc ctg cta tgg gtc cca      48
Met Glu Thr Asp Thr Leu Leu Leu Trp Val Leu Leu Leu Trp Val Pro
 1               5                  10                  15 gga tca acc gga gat att cag atg acc cag agt ccg tcg acc ctc tct      96
Gly Ser Thr Gly Asp Ile Gln Met Thr Gln Ser Pro Ser Thr Leu Ser
             20                  25                  30 gct agc gtc ggg gat agg gtc acc ata act tgc agg gca agt cag gac     144
Ala Ser Val Gly Asp Arg Val Thr Ile Thr Cys Arg Ala Ser Gln Asp
         35                  40                  45 att tcg aat tat tta aac tgg tat cag cag aag cca ggc aaa gct ccc     192
Ile Ser Asn Tyr Leu Asn Trp Tyr Gln Gln Lys Pro Gly Lys Ala Pro
     50                  55                  60 aag ctt cta att tat tac aca tca aga tta cac tca ggg gta cct tca     240
Lys Leu Leu Ile Tyr Tyr Thr Ser Arg Leu His Ser Gly Val Pro Ser
 65                  70                  75                  80 cgc ttc agt ggc agt gga tct ggg acc aat tat acc ctc aca atc tcg     288
Arg Phe Ser Gly Ser Gly Ser Gly Thr Asn Tyr Thr Leu Thr Ile Ser
                 85                  90                  95 agt ctg cag cca gat gat ttc gcc act tat ttt tgc caa cag ggt agt     336
Ser Leu Gln Pro Asp Asp Phe Ala Thr Tyr Phe Cys Gln Gln Gly Ser
            100                 105                 110 acg ctt ccg tgg acg ttc ggt cag ggg acc aag gtg gag gtc aaa         381
Thr Leu Pro Trp Thr Phe Gly Gln Gly Thr Lys Val Glu Val Lys
        115                 120                 125

<210> SEQ ID NO 6
<211> LENGTH: 127
<212> TYPE: PRT
<213> ORGANISM: Homo sapiens

<400> SEQUENCE: 6

Met Glu Thr Asp Thr Leu Leu Leu Trp Val Leu Leu Leu Trp Val Pro
 1               5                  10                  15

Gly Ser Thr Gly Asp Ile Gln Met Thr Gln Ser Pro Ser Thr Leu Ser
             20                  25                  30

Ala Ser Val Gly Asp Arg Val Thr Ile Thr Cys Arg Ala Ser Gln Asp
```

```
                   35                  40                  45
Ile Ser Asn Tyr Leu Asn Trp Tyr Gln Gln Lys Pro Gly Lys Ala Pro
         50                  55                  60

Lys Leu Leu Ile Tyr Tyr Thr Ser Arg Leu His Ser Gly Val Pro Ser
 65                  70                  75                  80

Arg Phe Ser Gly Ser Gly Ser Gly Thr Asn Tyr Thr Leu Thr Ile Ser
                 85                  90                  95

Ser Leu Gln Pro Asp Asp Phe Ala Thr Tyr Phe Cys Gln Gln Gly Ser
             100                 105                 110

Thr Leu Pro Trp Thr Phe Gly Gln Gly Thr Lys Val Glu Val Lys
         115                 120                 125

<210> SEQ ID NO 7
<211> LENGTH: 408
<212> TYPE: DNA
<213> ORGANISM: Homo sapiens
<220> FEATURE:
<221> NAME/KEY: CDS
<222> LOCATION: (1)..(408)

<400> SEQUENCE: 7 atg gat tgg gtg tgg acc ttg cta ttc ctg ata gct gca gcc caa agt    48
Met Asp Trp Val Trp Thr Leu Leu Phe Leu Ile Ala Ala Ala Gln Ser
 1               5                  10                  15 gcc caa gca cag gtc cag ttg gtg cag tct gga gct gag gtg aag aag    96
Ala Gln Ala Gln Val Gln Leu Val Gln Ser Gly Ala Glu Val Lys Lys
                 20                  25                  30 cct gga agc tca gtc aag gtg tcc tgc aaa gct tct ggg tat acc ttc   144
Pro Gly Ser Ser Val Lys Val Ser Cys Lys Ala Ser Gly Tyr Thr Phe
         35                  40                  45 aca gaa tat cca atg cac tgg gtg aga cag gct cca gga cag ggt ttc   192
Thr Glu Tyr Pro Met His Trp Val Arg Gln Ala Pro Gly Gln Gly Phe
 50                  55                  60 aag tgg atg ggc atg ata tac acc gac act gga gag cca tca tat gct   240
Lys Trp Met Gly Met Ile Tyr Thr Asp Thr Gly Glu Pro Ser Tyr Ala
 65                  70                  75                  80 gaa gag ttc aag gga cgg ttt aca ttc act ttg gac acc tct acc aac   288
Glu Glu Phe Lys Gly Arg Phe Thr Phe Thr Leu Asp Thr Ser Thr Asn
                 85                  90                  95 act gcc tat atg gag ctc agc tct ctc agg tct gag gac acg gct gtc   336
Thr Ala Tyr Met Glu Leu Ser Ser Leu Arg Ser Glu Asp Thr Ala Val
             100                 105                 110 tat tac tgt gta aga ttt tac tgg gat tac ttt gac tac tgg ggt caa   384
Tyr Tyr Cys Val Arg Phe Tyr Trp Asp Tyr Phe Asp Tyr Trp Gly Gln
         115                 120                 125 ggt acc ctg gtc aca gtc tcc tca                                    408
Gly Thr Leu Val Thr Val Ser Ser
         130                 135

<210> SEQ ID NO 8
<211> LENGTH: 136
<212> TYPE: PRT
<213> ORGANISM: Homo sapiens

<400> SEQUENCE: 8

Met Asp Trp Val Trp Thr Leu Leu Phe Leu Ile Ala Ala Ala Gln Ser
 1               5                  10                  15

Ala Gln Ala Gln Val Gln Leu Val Gln Ser Gly Ala Glu Val Lys Lys
                 20                  25                  30

Pro Gly Ser Ser Val Lys Val Ser Cys Lys Ala Ser Gly Tyr Thr Phe
```

```
                    35                  40                  45
Thr Glu Tyr Pro Met His Trp Val Arg Gln Ala Pro Gly Gln Gly Phe
        50                  55                  60

Lys Trp Met Gly Met Ile Tyr Thr Asp Thr Gly Glu Pro Ser Tyr Ala
 65                  70                  75                  80

Glu Glu Phe Lys Gly Arg Phe Thr Phe Thr Leu Asp Thr Ser Thr Asn
                85                  90                  95

Thr Ala Tyr Met Glu Leu Ser Ser Leu Arg Ser Glu Asp Thr Ala Val
            100                 105                 110

Tyr Tyr Cys Val Arg Phe Tyr Trp Asp Tyr Phe Asp Tyr Trp Gly Gln
        115                 120                 125

Gly Thr Leu Val Thr Val Ser Ser
    130                 135

<210> SEQ ID NO 9
<211> LENGTH: 1182
<212> TYPE: DNA
<213> ORGANISM: Homo sapiens
<220> FEATURE:
<221> NAME/KEY: CDS
<222> LOCATION: (36)..(1169)

<400> SEQUENCE: 9
ttttcttcca tttcaggtgt cgtgaggaat tcacc atg ctg ggc atc tgg acc         53
                                      Met Leu Gly Ile Trp Thr
                                        1               5 ctc cta cct ctg gtt ctg act agt gtc gct act cag aac ttg gaa ggc       101
Leu Leu Pro Leu Val Leu Thr Ser Val Ala Thr Gln Asn Leu Glu Gly
             10                  15                  20 ctg cat cat gat ggc caa ttc tgc cat aag ccc tgt cct cca ggt gaa       149
Leu His His Asp Gly Gln Phe Cys His Lys Pro Cys Pro Pro Gly Glu
         25                  30                  35 agg aaa gct agg gac tgc aca gtc aat ggg gat gaa cca gac tgc gtg       197
Arg Lys Ala Arg Asp Cys Thr Val Asn Gly Asp Glu Pro Asp Cys Val
     40                  45                  50 ccc tgc caa gaa ggg aag gag tac aca gac aaa gcc cat ttt tct tcc       245
Pro Cys Gln Glu Gly Lys Glu Tyr Thr Asp Lys Ala His Phe Ser Ser
 55                  60                  65                  70 aaa tgc aga aga tgt aga ttg tgt gat gaa gga cat ggc tta gaa gtg       293
Lys Cys Arg Arg Cys Arg Leu Cys Asp Glu Gly His Gly Leu Glu Val
                 75                  80                  85 gaa ata aac tgc acc cgg acc cag aat acc aag tgc aga tgt aaa cca       341
Glu Ile Asn Cys Thr Arg Thr Gln Asn Thr Lys Cys Arg Cys Lys Pro
             90                  95                 100 aac ttt ttt tgt aac tct act gta tgt gaa cac tgt gac cct tgc acc       389
Asn Phe Phe Cys Asn Ser Thr Val Cys Glu His Cys Asp Pro Cys Thr
        105                 110                 115 aaa tgt gaa cat gga atc atc aag gaa tgc aca ctc acc agc aac acc       437
Lys Cys Glu His Gly Ile Ile Lys Glu Cys Thr Leu Thr Ser Asn Thr
    120                 125                 130 aag tgc aaa gag gaa gga tcc aga tct aac gag ccc aaa tct tgt gac       485
Lys Cys Lys Glu Glu Gly Ser Arg Ser Asn Glu Pro Lys Ser Cys Asp
135                 140                 145                 150 aaa act cac aca tgc cca ccg tgc cca gca cct gaa ctc ctg ggg gga       533
Lys Thr His Thr Cys Pro Pro Cys Pro Ala Pro Glu Leu Leu Gly Gly
                155                 160                 165 ccg tca gtc ttc ctc ttc ccc cca aaa ccc aag gac acc ctc atg atc       581
Pro Ser Val Phe Leu Phe Pro Pro Lys Pro Lys Asp Thr Leu Met Ile
            170                 175                 180
```

-continued

| | | |
|---|---|---|
| tcc cgg acc cct gag gtc aca tgc gtg gtg gtg gac gtg agc cac gaa<br>Ser Arg Thr Pro Glu Val Thr Cys Val Val Val Asp Val Ser His Glu<br>     185                  190               195 | 629 |
| gac cct gag gtc aag ttc aac tgg tac gtg gac ggc gtg gag gtg cat<br>Asp Pro Glu Val Lys Phe Asn Trp Tyr Val Asp Gly Val Glu Val His<br>200                   205                  210 | 677 |
| aat gcc aag aca aag ccg cgg gag gag cag tac aac agc acg tac cgt<br>Asn Ala Lys Thr Lys Pro Arg Glu Glu Gln Tyr Asn Ser Thr Tyr Arg<br>215                 220              225           230 | 725 |
| gtg gtc agc gtc ctc acc gtc ctg cac cag gac tgg ctg aat ggc aag<br>Val Val Ser Val Leu Thr Val Leu His Gln Asp Trp Leu Asn Gly Lys<br>                235               240                245 | 773 |
| gag tac aag tgc aag gtc tcc aac aaa gcc ctc cca gcc ccc atc gag<br>Glu Tyr Lys Cys Lys Val Ser Asn Lys Ala Leu Pro Ala Pro Ile Glu<br>          250                  255               260 | 821 |
| aaa acc atc tcc aaa gcc aaa ggg cag ccc cga gaa cca cag gtg tac<br>Lys Thr Ile Ser Lys Ala Lys Gly Gln Pro Arg Glu Pro Gln Val Tyr<br>               265              270             275 | 869 |
| acc ctg ccc cca tcc cgg gat gag ctg acc aag aac cag gtc agc ctg<br>Thr Leu Pro Pro Ser Arg Asp Glu Leu Thr Lys Asn Gln Val Ser Leu<br>280                   285              290 | 917 |
| acc tgc ctg gtc aaa ggc ttc tat ccc agc gac atc gcc gtg gag tgg<br>Thr Cys Leu Val Lys Gly Phe Tyr Pro Ser Asp Ile Ala Val Glu Trp<br>295                   300              305           310 | 965 |
| gag agc aat ggg cag ccg gag aac aac tac aag acc acg cct ccc gtg<br>Glu Ser Asn Gly Gln Pro Glu Asn Asn Tyr Lys Thr Thr Pro Pro Val<br>                315               320                325 | 1013 |
| ctg gac tcc gac ggc tcc ttc ttc ctc tac agc aag ctc acc gtg gac<br>Leu Asp Ser Asp Gly Ser Phe Phe Leu Tyr Ser Lys Leu Thr Val Asp<br>         330                  335               340 | 1061 |
| aag agc agg tgg cag cag ggg aac gtc ttc tca tgc tcc gtg atg cat<br>Lys Ser Arg Trp Gln Gln Gly Asn Val Phe Ser Cys Ser Val Met His<br>               345               350              355 | 1109 |
| gag gct ctg cac aac cac tac acg cag aag agc ctc tcc ctg tct ccg<br>Glu Ala Leu His Asn His Tyr Thr Gln Lys Ser Leu Ser Leu Ser Pro<br>360                   365              370 | 1157 |
| ggt aaa tga tag ggtaccttct gag<br>Gly Lys<br>375 | 1182 |

<210> SEQ ID NO 10
<211> LENGTH: 376
<212> TYPE: PRT
<213> ORGANISM: Homo sapiens

<400> SEQUENCE: 10

Met Leu Gly Ile Trp Thr Leu Leu Pro Leu Val Leu Thr Ser Val Ala
1                 5                        10                 15

Thr Gln Asn Leu Glu Gly Leu His His Asp Gly Gln Phe Cys His Lys
                   20                       25                       30

Pro Cys Pro Pro Gly Glu Arg Lys Ala Arg Asp Cys Thr Val Asn Gly
                   35                       40                       45

Asp Glu Pro Asp Cys Val Pro Cys Gln Glu Gly Lys Glu Tyr Thr Asp
       50                       55                       60

Lys Ala His Phe Ser Ser Lys Cys Arg Arg Cys Arg Leu Cys Asp Glu
65                70                      75                       80

Gly His Gly Leu Glu Val Glu Ile Asn Cys Thr Arg Thr Gln Asn Thr
                   85                       90                       95

Lys Cys Arg Cys Lys Pro Asn Phe Phe Cys Asn Ser Thr Val Cys Glu

-continued

```
            100                 105                 110
His Cys Asp Pro Cys Thr Lys Cys Glu His Gly Ile Ile Lys Glu Cys
        115                 120                 125
Thr Leu Thr Ser Asn Thr Lys Cys Lys Glu Glu Gly Ser Arg Ser Asn
    130                 135                 140
Glu Pro Lys Ser Cys Asp Lys Thr His Thr Cys Pro Pro Cys Pro Ala
145                 150                 155                 160
Pro Glu Leu Leu Gly Gly Pro Ser Val Phe Leu Phe Pro Pro Lys Pro
                165                 170                 175
Lys Asp Thr Leu Met Ile Ser Arg Thr Pro Glu Val Thr Cys Val Val
            180                 185                 190
Val Asp Val Ser His Glu Asp Pro Glu Val Lys Phe Asn Trp Tyr Val
        195                 200                 205
Asp Gly Val Glu Val His Asn Ala Lys Thr Lys Pro Arg Glu Glu Gln
    210                 215                 220
Tyr Asn Ser Thr Tyr Arg Val Val Ser Val Leu Thr Val Leu His Gln
225                 230                 235                 240
Asp Trp Leu Asn Gly Lys Glu Tyr Lys Cys Lys Val Ser Asn Lys Ala
                245                 250                 255
Leu Pro Ala Pro Ile Glu Lys Thr Ile Ser Lys Ala Lys Gly Gln Pro
            260                 265                 270
Arg Glu Pro Gln Val Tyr Thr Leu Pro Pro Ser Arg Asp Glu Leu Thr
        275                 280                 285
Lys Asn Gln Val Ser Leu Thr Cys Leu Val Lys Gly Phe Tyr Pro Ser
    290                 295                 300
Asp Ile Ala Val Glu Trp Glu Ser Asn Gly Gln Pro Glu Asn Asn Tyr
305                 310                 315                 320
Lys Thr Thr Pro Pro Val Leu Asp Ser Asp Gly Ser Phe Phe Leu Tyr
                325                 330                 335
Ser Lys Leu Thr Val Asp Lys Ser Arg Trp Gln Gln Gly Asn Val Phe
            340                 345                 350
Ser Cys Ser Val Met His Glu Ala Leu His Asn His Tyr Thr Gln Lys
        355                 360                 365
Ser Leu Ser Leu Ser Pro Gly Lys
    370                 375
```

<210> SEQ ID NO 11
<211> LENGTH: 531
<212> TYPE: DNA
<213> ORGANISM: Homo sapiens
<220> FEATURE:
<221> NAME/KEY: CDS
<222> LOCATION: (36)..(518)

<400> SEQUENCE: 11

```
ttttcttcca tttcaggtgt cgtgaggaat tcacc atg ctg ggc atc tgg acc         53
                                      Met Leu Gly Ile Trp Thr
                                        1               5 ctc cta cct ctg gtt ctg act agt gtc gct act cag aac ttg gaa ggc       101
Leu Leu Pro Leu Val Leu Thr Ser Val Ala Thr Gln Asn Leu Glu Gly
            10                  15                  20 ctg cat cat gat ggc caa ttc tgc cat aag ccc tgt cct cca ggt gaa       149
Leu His His Asp Gly Gln Phe Cys His Lys Pro Cys Pro Pro Gly Glu
        25                  30                  35 agg aaa gct agg gac tgc aca gtc aat ggg gat gaa cca gac tgc gtg       197
Arg Lys Ala Arg Asp Cys Thr Val Asn Gly Asp Glu Pro Asp Cys Val
    40                  45                  50
```

```
ccc tgc caa gaa ggg aag gag tac aca gac aaa gcc cat ttt tct tcc      245
Pro Cys Gln Glu Gly Lys Glu Tyr Thr Asp Lys Ala His Phe Ser Ser
 55                  60                  65                  70 aaa tgc aga aga tgt aga ttg tgt gat gaa gga cat ggc tta gaa gtg      293
Lys Cys Arg Arg Cys Arg Leu Cys Asp Glu Gly His Gly Leu Glu Val
                 75                  80                  85 gaa ata aac tgc acc cgg acc cag aat acc aag tgc aga tgt aaa cca      341
Glu Ile Asn Cys Thr Arg Thr Gln Asn Thr Lys Cys Arg Cys Lys Pro
                     90                  95                 100 aac ttt ttt tgt aac tct act gta tgt gaa cac tgt gac cct tgc acc      389
Asn Phe Phe Cys Asn Ser Thr Val Cys Glu His Cys Asp Pro Cys Thr
            105                 110                 115 aaa tgt gaa cat gga atc atc aag gaa tgc aca ctc acc agc aac acc      437
Lys Cys Glu His Gly Ile Ile Lys Glu Cys Thr Leu Thr Ser Asn Thr
120                 125                 130 aag tgc aaa gag gaa gga tcc aga tct aac gag ccc aaa tct tgt gac      485
Lys Cys Lys Glu Glu Gly Ser Arg Ser Asn Glu Pro Lys Ser Cys Asp
135                 140                 145                 150 aaa act cac aca tgc cca ccg tgc cca tag tga ggtaccttct gag           531
Lys Thr His Thr Cys Pro Pro Cys Pro
                155

<210> SEQ ID NO 12
<211> LENGTH: 159
<212> TYPE: PRT
<213> ORGANISM: Homo sapiens

<400> SEQUENCE: 12

Met Leu Gly Ile Trp Thr Leu Leu Pro Leu Val Leu Thr Ser Val Ala
 1               5                  10                  15

Thr Gln Asn Leu Glu Gly Leu His His Asp Gly Gln Phe Cys His Lys
                 20                  25                  30

Pro Cys Pro Pro Gly Glu Arg Lys Ala Arg Asp Cys Thr Val Asn Gly
             35                  40                  45

Asp Glu Pro Asp Cys Val Pro Cys Gln Glu Gly Lys Glu Tyr Thr Asp
         50                  55                  60

Lys Ala His Phe Ser Ser Lys Cys Arg Arg Cys Arg Leu Cys Asp Glu
 65                  70                  75                  80

Gly His Gly Leu Glu Val Glu Ile Asn Cys Thr Arg Thr Gln Asn Thr
                 85                  90                  95

Lys Cys Arg Cys Lys Pro Asn Phe Phe Cys Asn Ser Thr Val Cys Glu
            100                 105                 110

His Cys Asp Pro Cys Thr Lys Cys Glu His Gly Ile Ile Lys Glu Cys
        115                 120                 125

Thr Leu Thr Ser Asn Thr Lys Cys Lys Glu Glu Gly Ser Arg Ser Asn
    130                 135                 140

Glu Pro Lys Ser Cys Asp Lys Thr His Thr Cys Pro Pro Cys Pro
145                 150                 155
```

***

METHOD OF TREATING GRAFT VERSUS HOST DISEASE BY ADMINISTRATION OF A FAS ANTAGONIST

This Application is a divisional of application No. 09/297,328, filed on Apr. 29, 1999 and for which priority is claimed under 35 U.S.C. § 120. Application Ser. No. 09/297,328 now abandoned is the national phase of PCT International Application No. PCT/JP97/03978 filed on Oct. 31, 1997 under 35 U.S.C. § 371. The entire contents of each of the above-identified applications are hereby incorporated by reference. This application also claims priority of Application Nos. 08-290459; 08-351718; and 09-262521 filed in JAPAN on Oct. 31, 1996; Dec. 27, 1996; and Sep. 26, 1997, respectively, under 35 U.S.C. § 119.

TECHNICAL FIELD

The present invention relates to a prophylactic/therapeutic agent for a disease containing a Fas antagonist as its effective component; a cell apoptosis-inhibitory agent; and an organ preservative agent.

BACKGROUND TECHNOLOGY

Fas is a cell surface antigen which transmits an apoptosis signal to the cell, and Fas is recognized by Fas antibody (Yonehara, S. et al., J. Exp. Med. vol. 169, 1747–1756, 1989), which is a monoclonal antibody produced by immunizing a mouse with human fibroblast. Fas gene was recently cloned by Itoh, N. et al., and it was then found out that Fas is a cell membrane protein of about 45 kD, and from the amino acid sequence, it was revealed that Fas is a member of the TNF receptor family (Cell, vol. 66, pages 233–243, 1991). The mouse Fas gene was also cloned (Watanabe-Fukunaga, R. et al., J. Immunol., vol. 148, pages 1274–1279, 1992), and its expression in thymus, liver, lung, heart, ovary was confirmed.

Human Fas ligand is a polypeptide which has been reported by Nagata et al. to be a biological molecule which induces apoptosis of Fas-expressing cells (Tomohiro Takahashi et al., International Immunology, vol. 6, pages 1567–1574, 1994). Human Fas ligand is a Type II membrane protein of the TNF family with a molecular weight of about 40 kD. As in the case of TNF, human Fas ligand in the human body is estimated to be in the form of a trimer (Masato Tanaka et al., EMBO Journal, vol. 14, pages 1129–1135, 1995). The extracellular domain of human Fas ligand is highly homologous with the extracellular domain of rat Fas ligand (Takashi Suda et al., Cell, vol. 75, pages 1169–1178, 1993) and mouse Fas ligand (Tomohiro Takahashi et al., Cell, vol. 76, pages 969–976, 1994). Human Fas ligand recognizes not only human Fas but also mouse Fas to induce apoptosis; and vice versa, rat Fas ligand and mouse Fas ligand also recognize human Fas to induce apoptosis.

Considerable researches have also been done on the mechanism of signal transduction in the cell upon Fas-mediated apoptosis, and identification and cloning of the factor which interacts with the intracellular domain of Fas, in particular, the region called "death domain" to transmit or block the signal has been reported. Possibility of the involvement of interleukin-1-converting enzyme (ICE)-related thiol proteases in Fas-mediated apoptosis has also been indicated.

A relationship between apoptosis, in particular, Fas-mediated apoptosis with various diseases and physiological phenomena has been recently indicated. For example, possibility has been indicated for involvement of abnormal Fas-mediated apoptosis in the decline of the T cell count in patients suffering from AIDS, in the death of hepatocytes in viral fulminant hepatitis, in some types of autoimmune diseases, and the like.

Involvement of the Fas/Fas ligand system in functions other than apoptosis has also been indicated. For example, the possibility has been indicated for the Fas/Fas ligand system to react with neutrophils to develop a proinflammatory action (Kayagaki, N. et al., Rinshou Meneki (Clinical Immunology), vol. 28, pages 667–675, 1996).

The condition wherein neutrophils and other immunocompetent cells are activated by various stimuli, such as endotoxins or by invasion, and humoral factors, such as cytokines are released into the blood and the tissues to induce systemic inflammatory responses is referred as systemic inflammatory response syndrome (hereinafter abbreviated as SIRS). SIRS is often associated with various organ failures, and when such organ failures are serious, SIRS may result in multiple organ failure syndrome (MODS) (Wakabayashi et al., Rinsho Kensa (Laboratory test), vol. 38, pages 349–352, 1994). Various factors are said to be involved in the process of organ failure, and the role in such organ failure of the invasion and accumulation of neutrophils by the action of IL-8 produced in macrophages and of other cells by IL-1 locally produced in response to invasion is of current interest. As described above, the Fas/Fas ligand system (hereinafter referred to as Fas/FasL system) is also reported for the possibility of its involvement in the activation of the neutrophils.

Ischemic reperfusion injury is found in practically all tissues and organs, and is involved in various diseases. Ischemic reperfusion injury is also a problem in preservation and transplantation of organs. Among such ischemic reperfusion injuries, those associated with infarction of liver, heart or kidney and those associated with surgery or transplantation, and in particular, tissue injury (such as cell necrosis) and dysfunction (such as cardiac arrhythmia) in the particular organ may lead to the death of the individual when they are serious, and therefore, such cases are a serious social problem. Various organ failures and ischemic reperfusion injuries from the early stage to the late stage are known to be associated with production and secretion of IL-8. It is also known that organ preservation and reperfusion in the course of organ transplantation is associated with the occurrence of the apoptosis. In addition, observation of apoptosis and fluctuation in the expression of Fas or FasL have been reported for some experimental models. There have also been reported a marked increase in the number of neutrophils at 24 hours after the reperfusion of liver after ischemia, and improvement of ischemic reperfusion injury by a neutralizing antibody of neutrophils (Jaeschke, H. et al., FASEB Journal, vol. 4, pages 3355–3359, 1990), and a marked increase of IL-8, neutrophils and macrophages at 3 hours after the reperfusion of the lung after ischemia, and improvement of ischemic reperfusion injury by a neutralizing antibody of the IL-8 (Sekido, N. et al., Nature, vol. 365, pages 654–657, 1993). These findings suggest significant roles of neutrophils and IL-8 in organ failures and ischemic reperfusion injuries of from the early stage to the late stage. On the other hand, it is not yet found how Fas/FasL is involved in such failures and injuries.

In infection by bacteria, endotoxin induces production of various cytokines in the body resulting in, for example, endotoxin shock in endotoxemia and sepsis as well as various organ damages including liver damage (Dinarello, C. A. et al., J. American Medical Association, vol. 269, page 1829, 1993), and serious conditions are more than often induced. Observation of apoptosis in such processes and the possibility of some involvement in such processes of Fas/FasL have been reported in experimental studies. However, it is not yet found how Fas/FasL is involved in such failures.

Death of cardiomyocytes in the case of a heart disease has been believed to occur mainly through necrosis. However, possibility of some involvement of apoptosis, and in particular, involvement of Fas-mediated apoptosis in such heart disease is now reported for clinical practices and in experiments. For example, it has been reported that the level of Fas expression increases when neonatal rat cardiomyocytes are placed in in vitro ischemic conditions (Tanaka, M. et al., Circ. Res., 75, 426–433, 1994); and that NO may have some relation to the remodeling of plaques in arteriosclerosis since IL-1 induces not only the synthesis of nitrogen monoxide (NO) of vascular smooth muscle cells but also apoptosis, apoptosis by IL-1 is inhibited by an inhibitor of NO synthesis, and Fas expression is induced by NO (Fukuo, K. et al., Hypertension, 27, 823–826, 1996). It has also been reported that apoptosis of cardiomyocytes is found in a canine heart failure model and such apoptosis is associated with an increased Fas expression (Lab. Invest., 73, 771–787, 1995), and that most of the cardiomyocyte death in canine the myocardial infarction model occurs through apoptosis, and such cardiomyocyte death is associated with a 100-fold increase in Fas expression (Lab. Invest., 74, 86–107, 1996). Furthermore, Fukuda et al. examined Fas expression in cardiomyocytes of cardiomyocardial disease patients, and found no Fas expression in hypertrophic cardiomyopathy but some Fas expression in at least a part of cardiomyocytes in cases of myocarditis and dilated cardiomyopathy (Idiopathic Cardiomyopathy Investigation Group, 1994 Business Year Research Report, 152–155, 1995). However, it is yet to be found out how Fas is involved in such heart diseases. Accordingly, the reports as described above have provided no data with regard to whether Fas acts to promote the apoptosis of the cardiomyocytes or to suppress the apoptosis of the cardiomyocytes in heart diseases, and it was still unclear whether Fas is directly involved in cytotoxicity or death of the cardiomyocytes of the patients suffering from heart diseases. As a consequence, no therapeutic agent and no therapy for heart disease wherein the disease, is treated by inhibiting the Fas-mediated apoptosis is known to date.

Involvement of apoptosis is also indicated for renal diseases, and increase in Fas mRNA expression is reported in an experimental model of renal ischemic reperfusion injury (Haruno, N. et al., Endocrinology, vol. 137, 1938–1948, 1996). However, it is yet to be found out how the Fas/FasL system is involved in such renal diseases.

Graft versus host disease (hereinafter referred to as GVHD) is a disease caused by graft versus host reaction (GVH reaction), which is an immunoreaction that may occur upon transplantation of lymphocytes of a donor or a graft, against the tissue antigens of the host. Exemplary GVHDs are GVHD after bone marrow transplantation, such as with incompatible bone marrow transplantation or with bone marrow transplantation in congenital immune deficiency syndrome; GVHD after organ transplantation; GVHD after blood transfusion, in which a large amount of blood is transfused to a patient of hypoimmunity; and the like. GVHD is associated with organ or tissue failure based on GVH reaction, and diarrhea, exhaustion such as weight loss and thinning, exanthem, splenomegaly, and liver dysfunction are clinically observed. GVHD is also associated with histological symptoms such as disorganization of bone marrow and lymphoid tissue and atrophy of intestinal villi.

Death of the cells constituting the host tissue in various GVHD has been believed to occur mainly through necrosis. However, the possibility of some involvement of apoptosis, and in particular, Fas-mediated apoptosis in such GVHD is now reported from experiments. For example, it has been reported that death of epithelial cells in intestine, skin and tongue in a mouse GVHD model occurs mainly through apoptosis (Aniti C. Gilliam et al., J. Invest. Dermatol., vol. 107, pages 377–383, 1996). With regard to the involvement of Fas-mediated apoptosis, it has been reported that no difference was found in survival time between cases when the donor was spleen lymphocytes from a control mouse with normal Fas ligand and cases when the donor was spleen lymphocytes from a gld mouse, which is a Fas ligand-mutated mouse, and practically no damage in skin and liver was induced (Matthew, B., Barker, B. et al., J. Exp. Med., vol. 183, 2645–2659, 1996). In spite of the indication of the involvement of Fas-mediated apoptosis in GVHD, there is no conclusion with regard to whether the Fas-mediated apoptosis is related to mortality with the GVHD. Furthermore, the report as described above utilizes spleen lymphocytes from a gld mouse for the material, and it is likely that the GVHD reaction is influenced by alteration in the amount of the expression of factors other than Fas ligand (such as perforin and TNF) as a substitute for the lack of Fas ligand, and the results obtained may not necessarily reflect the genuine effect of the lack of Fas ligand. Therefore, it is yet to be found out how Fas-mediated apoptosis is involved in GVHD, and whether a substance which specifically inhibits Fas-mediated apoptosis can be used as a therapeutic agent for GVHD.

Nonspecific immunosuppressives, such as cyclosporin, that have been used as a prophylactic or therapeutic agent of the GVHD generate nonspecific immunosuppression, and therefore, suffer from adverse side effects such as infections. No therapeutic agent and no therapy for GVHD wherein the GVHD is treated by inhibiting Fas-mediated apoptosis are known to date. In addition, no therapeutic agent and no therapy for GVHD wherein the GVHD is treated by utilizing selective immunosuppression are known to date.

With regard to diseases based on ischemic reperfusion injury, commercially available drugs mainly aim at thrombolysis and improvement of circulation, and no drug is available that directly prevents or treats the damage. With regard to the endotoxemia and sepsis, steroid and proteolytic enzyme inhibitor, for example, are used in the case of shock, and no drug is currently available that directly prevents or treats the organ damage. The drugs used for the diseases based on organ damage mainly aim at palliative treatment, and no drug is available that prevents or radically treats the diseases based on organ damage. In addition, no prophylactic or therapeutic agent which is widely effective for various tissues and organs is available.

In view of such situation, there is a demand for a pharmaceutical which is effective in preventing or treating diseases based on damage of the tissue or the organ in a wide variety of tissues or organs, which is effective in vivo, and which is less toxic to humans. However, no pharmaceutical is so far available that meets such requirements.

An object of the present invention is to provide a pharmaceutical and a therapy in the form of a prophylactic/therapeutic agent or an organ preservative agent which contains a Fas antagonist and which works through a new mechanism. More particularly, the present invention provides a prophylactic/therapeutic agent, an organ preservative agent, which contains a Fas antagonist, and a therapy, in which a Fas antagonist are used for diseases wherein Fas is involved.

SUMMARY OF THE INVENTION

The inventors of the present invention have conducted an intensive study on function of the Fas/Fas ligand system and the role of apoptosis mediated by the Fas/Fas ligand system in various diseases, and found that conditions may be improved in various disease models by suppressing the actions of the Fas/Fas ligand system, and in particular, by suppressing the Fas/Fas ligand system-mediated apoptosis; and that, for example, that death of cardiomyocytes upon reperfusion after ischemia, onset of the GVHD associated with allogenic bone marrow transplantation, and organ damages caused by endotoxin are suppressed by an antagonist which inhibits the Fas-mediated apoptosis. The present invention has been completed on the bases of such finding.

In other words, the present invention provides a drug, and in particular a drug for preventing and/or treating a disease, namely, a prophylactic/therapeutic agent which contains a Fas antagonist as its effective component, and which is adapted for use in a disease wherein the Fas/Fas ligand system is involved, and in particular, a disease wherein the Fas-mediated apoptosis is involved. The agent of the present invention may be used for such diseases as (1) heart diseases, and preferably, ischemic heart diseases, and especially, myocardial infarction; heart failure; and ischemic reperfusion injury; (2) renal diseases, and preferably, renal failure, renal ischemia, ischemic reperfusion injury, and acute renal failure; (3) GVHD; (4) diseases based on ischemia or ischemic reperfusion injury, and in particular, diseases based on ischemic reperfusion injury in heart, kidney, or liver; and diseases based on ischemic reperfusion injury associated with surgery or transplantation and ischemic reperfusion injury associated with thrombolytic therapy or angioplasty; (5) damages of organs caused by bacterial endotoxin, and endotoxemia, sepsis, and damages associated therewith; and in particular, liver damage and liver failure; and the like.

Another aspect of the present invention is an organ preservative agent characterized by its inclusion of a Fas antagonist. The present invention also provides an apoptosis inhibitory agent which contains a Fas antagonist as its effective component. The Fas antagonist is preferably at least one member selected from an anti-Fas ligand antibody, an anti-Fas antibody and a Fas derivative, and more particularly, the anti-Fas ligand antibody is preferably a humanized anti-Fas ligand antibody.

In other words, the present invention provides novel utilities of the Fas antagonist.

It should be noted that, in the present invention, a Fas antagonist is a substance which has a suppressive or inhibitory action, and more particularly, a substance which suppresses or inhibits the biological actions of the Fas/Fas ligand system, and in particular the Fas-mediated cell apoptosis.

BRIEF DESCRIPTION OF THE DRAWINGS

FIG. 1 is a view showing sequences of cDNA (SEQ ID NO: 1) and translated amino acid (SEQ ID NO: 2) for the variable region in the light chain of mouse F919-9-18 antibody. CDRs are underlined, and the first amino acid in the mature chain is underlined in duplicate.

FIG. 2 is a view showing sequences of cDNA (SEQ ID NO: 3) and translated amino acid (SEQ ID NO: 4) for the variable region in the heavy chain of mouse F919-9-18 antibody. CDRs are underlined, and the first amino acid in the mature chain is underlined in duplicate.

FIG. 3 is a view showing sequences of cDNA (SEQ ID NO: 5) and translated amino acid (SEQ ID NO: 6) for the variable region in the light chain of humanized F919 antibody. CDRs are underlined, and the first amino acid in the mature chain is underlined in duplicate.

FIG. 4 is a view showing sequences of cDNA (SEQ ID NO: 7) and translated amino acid (SEQ ID NO: 8) for the variable region in the heavy chain of humanized F919 antibody. CDRs are underlined, and the first amino acid in the mature chain is underlined in duplicate.

FIG. 5 is a view showing the nucleotide sequence (SEQ ID NO: 9) and the amino acid sequence (SEQ ID NO: 10) deduced therefrom of a part of a vector (pM1304) containing the nucleotide sequence of the cDNA coding for the shFas (nd29)-Fc which is a Fas derivative (to 64th amino acid (to 275th DNA)).

FIG. 6 is a view showing the nucleotide sequence (SEQ ID NO: 9) and the amino acid sequence (SEQ ID NO: 10) deduced therefrom of a part of the vector (pM1304) containing the nucleotide sequence of the cDNA coding for the shFas(nd29)-Fc which is a Fas derivative (from 65th amino acid to 144th amino acid (from 276th DNA to 515th DNA)). Possible N-glycosylation sites are marked with ★.

FIG. 7 is a view showing the nucleotide sequence (SEQ ID NO: 9) and the amino acid sequence (SEQ ID NO: 10) deduced therefrom of a part of the vector (pM1304) containing the nucleotide sequence of the cDNA coding for the shFas(nd29)-Fc which is a Fas derivative (from 145th amino acid to 224th amino acid (from 516th DNA to 755th DNA)). Possible N-glycosylation site is marked with ★.

FIG. 8 is a view showing the nucleotide sequence (SEQ ID NO: 9) and the amino acid sequence (SEQ ID NO: 10) deduced therefrom of a part of the vector (pM1304) containing the nucleotide sequence of the cDNA coding for the shFas(nd29)-Fc which is a Fas derivative (from 225th amino acid to 304th amino acid (from 756th DNA to 995th DNA)).

FIG. 9 is a view showing the nucleotide sequence (SEQ ID NO: 9) and the amino acid sequence (SEQ ID NO: 10) deduced therefrom of a part of the vector (pM1304) containing the nucleotide sequence of the cDNA coding for the shFas(nd29)-Fc which is a Fas derivative (from 305th amino acid (from 996th DNA)).

FIG. 10 is a view showing the nucleotide sequence (SEQ ID NO: 11) and the amino acid sequence (SEQ ID NO: 12) deduced therefrom of a part of a vector (pM1317) containing the nucleotide sequence of the cDNA coding for the shFas (nd29)-hinge which is a Fas derivative (to 64th amino acid (to 275th DNA)).

FIG. 11 is a view showing the nucleotide sequence (SEQ ID NO: 11) and the amino acid sequence (SEQ ID NO: 12) deduced therefrom of a part of the vector (pM1317) containing the nucleotide sequence of the cDNA coding for the shFas(nd29)-hinge which is a Fas derivative (from 65th amino acid (from 276th DNA to 515th DNA)). Possible N-glycosylation sites are marked with ★.

FIG. 12 is a view showing the nucleotide sequence (SEQ ID NO: 11) and the amino acid sequence (SEQ ID NO: 12) deduced therefrom of a part of the vector (pM1317) containing the nucleotide sequence of the cDNA coding for the shFas (nd29)-hinge which is a Fas derivative (from 516th DNA).

BEST MODE FOR CARRYING OUT THE INVENTION

Figure 13:
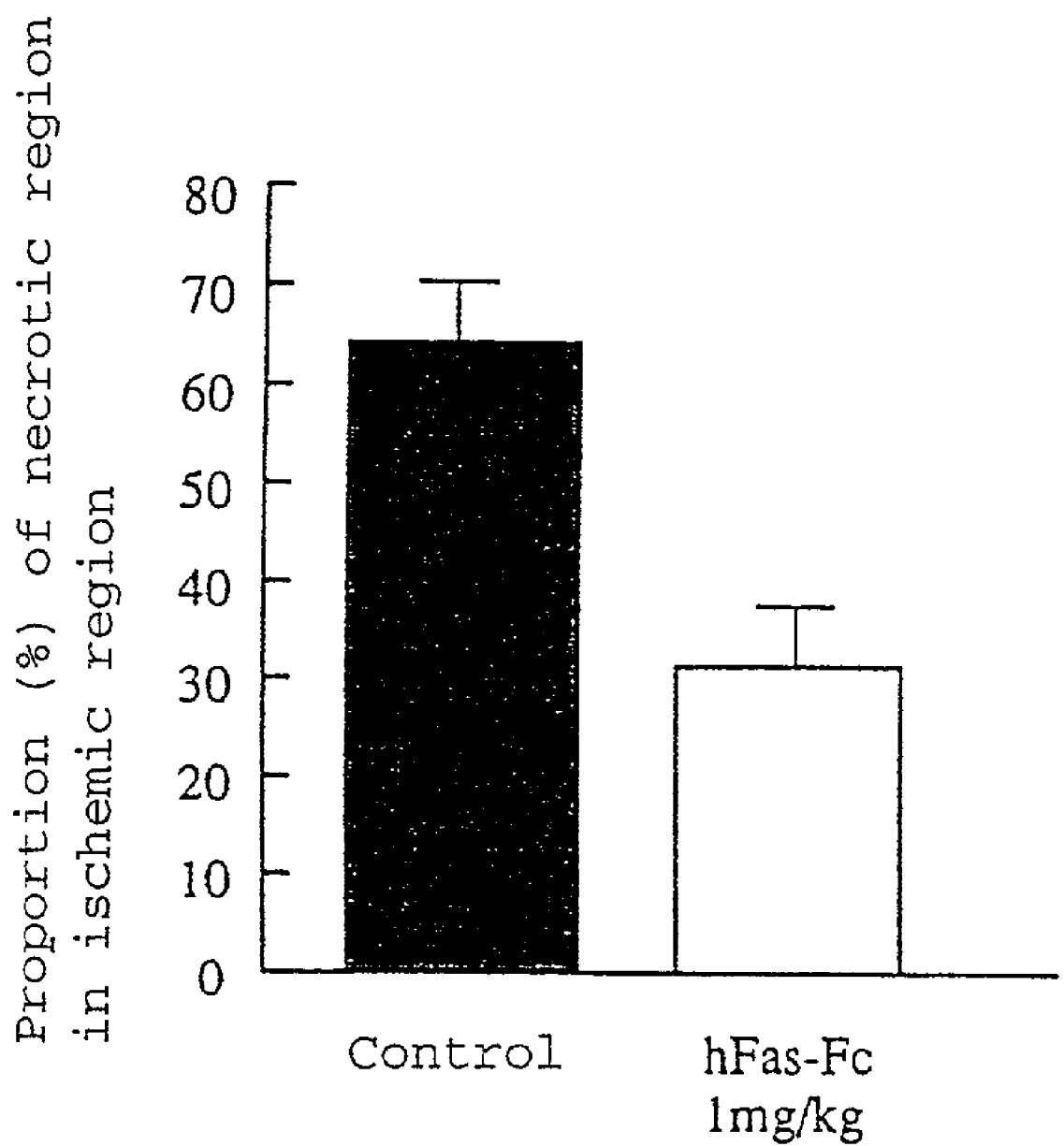
FIG. 13 is a view showing the suppressive effect of the Fas derivative (hFas-Fc) for myocardial infarction lesion in an experimental rat model of heart ischemic reperfusion injury.

Next, the present invention is described in further detail.

The prophylactic/therapeutic agent of the present invention may be used for various diseases wherein biological actions of the Fas/Fas ligand system, and in particular, the Fas mediated apoptosis are involved. In such diseases, the biological actions of the Fas/Fas ligand system, and in particular, the Fas mediated apoptosis relate to or contribute for the onset, remaining, or worsening of the symptoms or pathology of such diseases.

Exemplary such diseases are heart diseases, renal diseases, GVHD, ischemic reperfusion injury, and diseases caused by bacterial endotoxin. (1) Preferable exemplary heart diseases include ischemic heart diseases, and in particular, myocardial infarction; myocarditis caused by various factors; cardiomyopathy, and in particular, dilated cardiomyopathy; heart failure; and ischemic reperfusion injury and heart diseases caused by such ischemic reperfusion injury. The myocardial infarction include acute myocardial infarction and old myocardial infarction. The heart failure include the heart failure in ischemic heart diseases which often occur as a complication with the acute myocardial infarction or the old myocardial infarction.

(2) Exemplary GVHD include GVHD after bone marrow transplantation such as incompatible bone marrow transplantation and bone marrow transplantation in congenital immune deficiency; GVHD after organ transplantation; posttransfusional GVHD such as GVHD after blood transfusion of a large amount to a patient of hypoimmunity; and the like. GVHD is associated with organ or tissue failure based on GVH reaction, and diarrhea, exhaustion such as weight loss and thinning, exanthem, and liver dysfunction are observed. GVHD is also associated with histological symptoms such as disorganization of bone marrow and lymphoid tissue and atrophy of intestinal villi.

(3) Exemplary renal diseases include renal ischemia, renal ischemic reperfusion injury, diseases caused thereby, and renal failure and diseases causing the renal failure, and preferably, acute renal failure. The renal failure include prerenal acute renal failure, postrenal acute renal failure, and renal acute renal failure. The diseases causing the renal acute renal failure include acute tubule necrosis due to renal circulation failure or renal ischemia, acute tubule necrosis due to renal toxicity, acute glomerulonephritis, acute interstitial nephritis, and acute cortical necrosis.

(4) Exemplary diseases based on ischemia and ischemic reperfusion injury include, among others, diseases based on ischemic reperfusion injury of heart, kidney, liver, brain, lung, spleen or pancreas, and preferably, heart, kidney, or liver; diseases based on ischemic reperfusion injury associated with surgery or transplantation and ischemic reperfusion injury associated with thrombolytic therapy or angioplasty.

The term "ischemic reperfusion injury" designates injury of the tissue or dysfunction of organ or tissue which occurs upon restoration of blood flow (reperfusion) after localized complete loss of the blood flow (ischemia) by such causes as infarction, surgery, transplantation, thrombolytic therapy, angioplasty, and the like. The term "diseases based on ischemic reperfusion injury" includes the diseases found in liver, heart, kidney, brain, lung, spleen, pancreas, or the like including liver failure, reperfusion arrhythmia, and renal failure as well as conditions and pathology associated with such diseases.

(5) Exemplary diseases caused by endotoxin include injury of organs by the endotoxin, and endotoxemia or sepsis and diseases caused by the endotoxemia or sepsis such as liver damage, acute liver failure, renal damage, and renal failure.

(6) Diseases based on organ injury other than the above-mentioned diseases are also included within the diseases subject to the prophylactic/therapeutic agent of the present invention. The term "diseases based on organ injury" includes not only the organ failures such as liver failure and renal failure but also the conditions such as jaundice, increase in blood GPT, GOT, LDH and the like, fatigue, malaise, hypophagia, consciousness disorder, excitation, coma, ascites, decrease in filtration volume by glomerulus, edema, proteinuria, oliguria, hyperkalemia, metabolic acidosis, increase in blood creatinine and blood urea nitrogen, and the like associated with such diseases. MODS associated with SIRS are also included.

Other diseases which are subject to the prophylactic/therapeutic agent of the present invention are viral hepatitis and nonviral alcoholic or drug hepatitis.

In the diseases as described above, the Fas antagonist suppresses the apoptosis of the cells which compose the organ or the tissue, for example, apoptosis of cardiomyocytes.

According to another aspect of the present invention, there is provided a preservative for an organ such as heart, kidney or liver characterized by its inclusion of a Fas antagonist as its effective component.

It should be noted that the present invention is adapted for use in human, but also in animals other than human.

The Fas antagonist used in the present invention may be correctly referred to as an antagonist for the Fas/Fas ligand system, and the Fas antagonist is not limited to any particular type so long as it prevents or blocks the signal generation or transduction by the Fas at some stage, and it suppresses or inhibits the function or the biological action of the Fas/Fas ligand system, and in particular, the Fas-mediated apoptosis, and particularly, the Fas-mediated apoptosis by the Fas ligand. The Fas antagonist may act through various mechanisms, and exemplary Fas antagonists are those inhibiting the action or the function of the Fas ligand or the Fas; those interacting with the extracellular domain of the Fas ligand or the extracellular domain of the Fas; those inhibiting the interaction between the Fas ligand and the Fas; those affecting the interaction between the intracellular domain of the Fas and an intracellular factor which interacts therewith; those suppressing the activity of the intracytoplasmic factor (such as ICE-like protease) which is involved in the signal transduction of the Fas-mediated apoptosis; and the like. The Fas antagonists include both high molecular weight proteinaceous substance and low molecular weight compound. More illustratively, exemplary Fas antagonists used in the present invention include a Fas derivative, an anti-Fas ligand antibody, an anti-Fas antibody, an antisense oligonucleotide for the mRNA or the gene of the Fas or the Fas ligand, a substance which interacts with the intracellular domain of the Fas, an ICE inhibitor, and the like which are provided with the activity to inhibit the action of the Fas/FasL system, and in particular, the Fas-mediated apoptosis. Preferably, the Fas antagonist used in the present invention may be a Fas derivative, an anti-Fas antibody, or an anti-Fas ligand antibody which exhibits inhibitory action for the Fas-mediated apoptosis. In addition, the Fas and the Fas ligand are preferably of human origin; the anti-Fas antibody and the anti-Fas ligand antibody are preferably a human anti-Fas antibody and a human anti-Fas ligand antibody, respectively; and the anti-Fas ligand antibody is preferably a humanized anti-Fas ligand antibody. The humanized anti-Fas ligand antibody is preferably the one wherein the constant region and the framework region are of human origin, and the complementarity determining region are of non-human origin. The Fas antagonist used in the present invention is preferably the one which inhibits the apoptosis if the Fas-expressing cell in an appropriate assay described in International Patent Application Publication No. WO 95/13293 or the like.

It should be noted that the publications cited in the specification of the present invention are incorporated herein by reference.

The antibody used in the present invention may be either a polyclonal antibody or a monoclonal antibody, and the molecular species used in the present invention is not particularly limited. The antibody used in the present invention may be either an antibody molecule of normal form or a fragment thereof which is capable of binding to the antigen to inhibit the Fas antigen-mediated apoptosis, for example, Fab, F(ab')$_2$, Fv, or single chain Fv (scFv) which is the Fv of heavy chain linked to the Fv of light chain by an adequate linker to form a single chain. In addition, the antibody used in the present invention may be an immunoglobulin of any class, subclass or isotype. As described above, the antibody used in the present invention is not limited to any particular type as long as is capable of binding to the Fas ligand or the Fas antigen to inhibit the biological actions of the Fas/Fas ligand system, and in particular, the Fas antigen-mediated apoptosis.

The anti-Fas ligand antibody used in the present invention may be an antibody of any type (either monoclonal or polyclonal) and any origin produced by any appropriate process. The anti-Fas ligand antibody, however, is preferably a monoclonal antibody derived from a mammal. The monoclonal antibody used in the present invention may be produced in any animal species so long as it is a mammal which may be human or non-human. The monoclonal antibody from a mammal other than human may be the one from rabbit or other rodents. The non-limiting preferable examples of such rodents are mouse, rat and hamster, and use of such animals facilitates a convenient production of the monoclonal anti body. Furthermore, the monoclonal antibody may be the one which is capable of recognizing the antigen in a conventional immunoprocess such as radioimmunoassay (RIA), enzyme immunoassay (EIA, ELISA), immunofluorescent analysis, or the like, and whose activity of suppressing the apoptosis of the Fas antigen-expressing cell is measurable by an appropriate assay procedure described in International Patent Application Publication No. WO 95/13293, and the like.

Among these, an example of the most preferable anti-Fas ligand antibody is mouse F919-9-18 antibody produced by hybridoma F919-9-18 which was originally deposited on Jun. 22, 1995 in National Institute of Bioscience and Human Technology, Agency of Industrial Science and Technology (1-3, Higashi 1-chome, Tsukuba-shi, Ibaraki-ken, Japan) (Accession No. P-15002) and transferred from the original deposition to the international deposition on May 9, 1996 (Accession No. FERM BP-5535). The sequences of the variable regions of the antibody are shown in FIG. 1 (cDNA is described in SEQ. ID No. 1) and FIG. 2 (cDNA is described in SEQ. ID No. 3).

The anti-Fas ligand antibody and the anti-Fas antibody used in the present invention may be prepared, for example, by the process described in International Patent Application Publication No. WO 95/13293, International Patent Application No. PCT/JP96/01820, and International Patent Application Publication No. WO 95/10540.

When a monoclonal antibody is used in the present invention, such monoclonal antibody may be prepared by the process known in the art, for example, by using Fas antigen, Fas ligand, or a partial peptide thereof for the immunization antigen, immunizing an animal with such antigen in accordance with a conventional process, fusing the resulting immunized cell with a known parent cell by a conventional cell fusion process, and screening for the monoclonal antibody-producing cell by a conventional screening process.

More illustratively, when the immunization antigen is human Fas ligand or its fragment, the nucleotide sequence of the human Fas ligand disclosed in Takahashi, T. (International Immunology, vol. 6, pages 1567–1574, 1994) is used, and this nucleotide sequence is inserted in a known expression vector system to transform an adequate host cell, the desired Fas ligand protein is obtained by purification from the transformed cell or the culture supernatant of the transformed cell, and the thus obtained purified Fas ligand protein is used for the immunization antigen.

The mammal which is immunized with the immunization antigen is not limited to any particular type, and the mammal may be selected by considering the compatibility with the parent cell used in the cell fusion. Exemplary animals are mouse, rat, hamster, and rabbit.

The immunization of the animal with the immunization antigen may be carried out by a known procedure. After the immunization and confirmation of the increase of the serum level of the desired antibody, the immunocytes are isolated from the animal, and subjected to cell fusion. The preferable immunocytes are splenocytes.

The parent cell to be fused with the immunocyte is not limited to any particular type. However, use of known mammal myeloma cell lines, and in particular, a mouse myeloma cell line such as P3-X63-Ag8-U1 (P3-U1) is preferred. The cell fusion of the above-described immunocyte and the myeloma cell may be carried out basically in accordance with a known process such as the procedure of Milstein et al. (Milstein et al., Methods Enzymol. 73: 3–46, 1981).

The hybridoma is then screened for the one producing the target antibody used in the present invention and subsequently cloned.

The monoclonal antibody is obtained from the thus prepared hybridoma producing the monoclonal antibody used in the present invention by such procedures as cultivating the hybridoma according to the conventional method and obtaining the monoclonal antibody from the supernatant; or transplanting the hybridoma to a mammal compatible with the hybridoma for propagation, and obtaining the monoclonal antibody from the ascite of the mammal. The former procedure is adapted for producing the monoclonal antibody of high purity, and the latter procedure is adapted for producing the monoclonal antibody in a large amount.

The monoclonal antibody produced by such process for use in the present invention may be further purified by a known purification means such as salt precipitation, gel filtration, affinity chromatography, and the like.

The monoclonal antibody used in the present invention is not limited to the one produced by using a hybridoma, and may be the one produced by an antibody-producing cell immortalized by EBV and the like or the one produced by a genetic engineering procedure.

In addition, the anti-Fas ligand antibody or the anti-Fas antibody used in the present invention is preferably a chimeric antibody or a humanized antibody which is an antibody intentionally altered for the purpose of reducing heteroantigenicity to human.

The use of non-human monoclonal antibody such as mouse antibody is associated with defects when it is repeatedly used in treating a human. The first defect is that the mouse monoclonal antibody has a relatively short circulation halflife and when used for human, the mouse monoclonal antibody will not develop other important functional properties of the immunoglobulin.

The second defect is that the non-human monoclonal antibody includes a substantial length of amino acid which is immunogenic when injected into a human patient. More illustratively, it has been demonstrated by a number of studies that, after injection of a foreign antibody, an extremely strong immunoreaction against the antibody may be induced in the patient to essentially nullify the therapeutic effectivity of the antibody after the first treatment. Furthermore, if various mouse monoclonal antibodies or other monoclonal antibodies with the antigenicity against human are developed in future and one or more such non-human antibodies are used for once or for several times, the subsequent administration of such non-human antibody after such initial administration may be nullified due to the crossreactivity even if the subsequent therapy had no relation to the initial therapy. In some a case, the non-human antibody administered after the initial administration may even act as a hazardous substance.

An exemplary such chimeric antibody is a chimeric antibody comprising the variable region from the monoclonal antibody of a mammal other than human such as mouse, and the constant region from the human antibody. Such chimeric antibody may be produced by a known chimeric antibody production process, and in particular, by a genetic engineering process.

More preferably, the anti-Fas ligand antibody used in the present invention is a reshaped human antibody wherein complementarity determining region (CDR) of the human antibody is replaced with the complementarity determining region derived from the antibody of a mammal other than human such as mouse. More illustratively, the constant region and the framework region are preferably of human origin, and the complementarity determining region is preferably of non-human origin. A preferable example of the reshaped human antibody (humanized antibody) is humanized antibody having the CDR derived from the mouse F919-9-18 antibody, which is disclosed in International Patent Application Publication No. WO 97/02290 (Application No. PCT/JP96/01820). Examples of the variable regions is shown in FIG. 3 (cDNA is described in SEQ. ID No. 5) and FIG. 4 (cDNA is described in SEQ. ID No. 7).

It should be noted that, if necessary, an amino acid in the framework (FR) region in the variable region of the antibody may be substituted with another amino acid so that the complementarity determining region of the humanized antibody would form an adequate antigen-binding site.

The humanized antibody used in the present invention may be prepared in accordance with Leachman et al. (Nature 332: 323 (1988) and European Patent Publication No. EP-A-0239400); Queen et al. (Proc. Natl. Acad. Sci. USA 86: 10029 (1989), International Patent Application Publication Nos. WO 90/07861 and WO 92/11018); Co et al. (Proc. Natl. Acad. Sci. USA 88: 2869 (1991)); Co and Queen (Nature 351: 501 (1991)); Co et al. (J. Immunol. 148: 1149 (1992)), and the like.

The Fas derivative used in the present invention is not limited to any particular type as long as it is capable of binding at least with the Fas ligand, or capable of inhibiting the Fas ligand-mediated apoptosis. The Fas derivative may also be the one which comprises an amino acid sequence of a known Fas that has been arbitrarily mutated by substitution, deletion, addition or/and insertion, and which inhibits the biological actions of the Fas/Fas ligand system, and in particular, the Fas-mediated apoptosis, with the binding activity to the Fas ligand retained. The Fas derivative may also be a mutant of Fas, Fas in a truncated form, a chimeric protein, a fusion protein, and a chemically modified Fas. The Fas from which the Fas derivative is derived may be the one derived from any animal species, although use of the Fas of human origin is preferred in consideration of the antigenicity.

Figure 12:
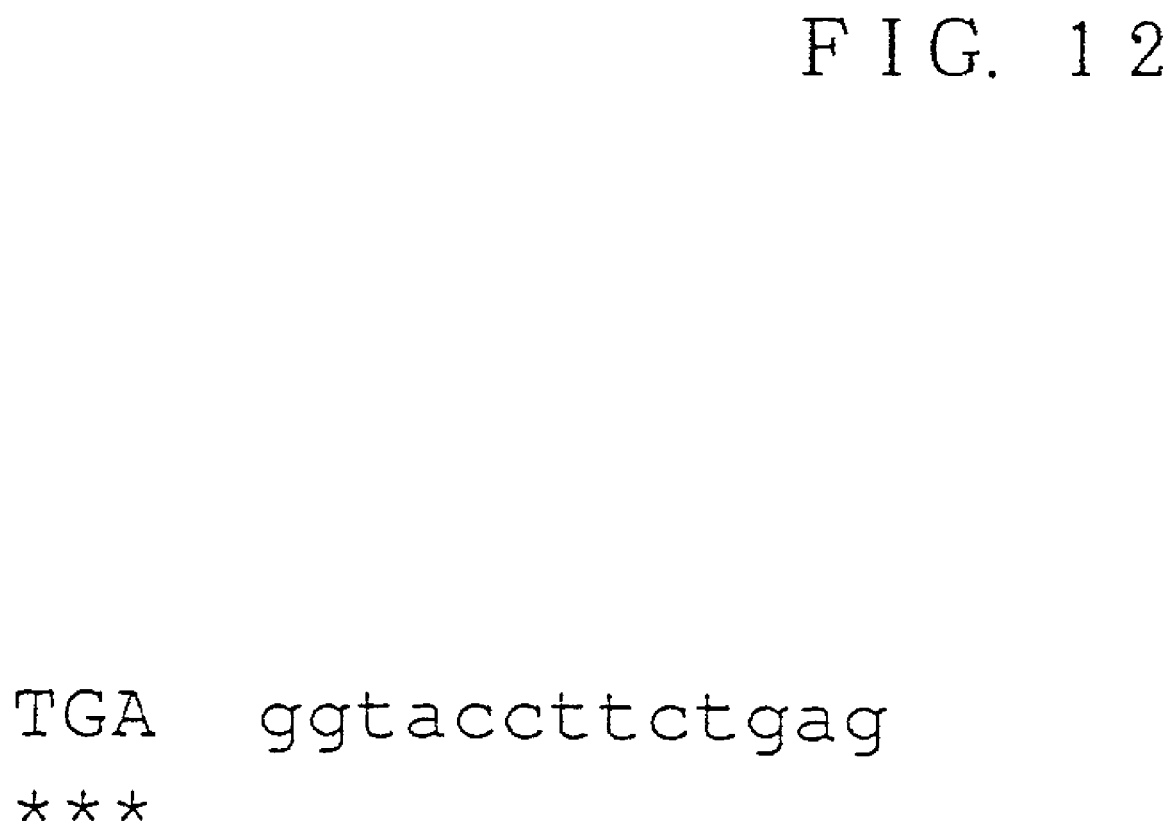

Exemplary Fas derivatives are the extracellular domain of a known Fas; a Fas antigen from which the transmembrane domain has been deleted; a chimeric protein of the extracellular domain of a Fas and another protein such as hFas-Fc which is a chimeric protein of the extracellular domain of human Fas and Fc fragment of human immunoglobulin. The Fas derivative may be the one prepared by any production process by utilizing known Fas sequences and known gene engineering techniques. For example, the process for producing the human Fas-Fc is described in the Examples of International Patent Application Publication No. WO 95/13293. Another preferable Fas derivative is the Fas having a deletion in its N terminal. A Fas derivative coded in plasmids (pM1304 and pM1317) included in the *E. coli* which were originally deposited on Mar. 14, 1996 in National Institute of Bioscience and Human Technology, Agency of Industrial Science and Technology (1-3, Higashi 1-chome, Tsukuba-shi, Ibaraki-ken, Japan) (Accession Nos. P-15514 and P-15515) and transferred from the original deposition to the international deposition on Mar. 6, 1997 (Accession No. FERM BP-5854 and Accession No. FERM BP-5855) (The accession Nos. in Taiwan were CCRC 940171 and CCRC 940170, respectively.) is a derivative including the extracellular domain of the known human Fas from which N terminal sequence of from 1st to 29th amino acid has been deleted, and this highly active derivative is a preferable example of the effective component for the prophylactic/therapeutic agent of the present invention (partial nucleotide sequences in the vector (pM1304) including the nucleotide sequence of the cDNA coding for shFas(nd29)-Fc are described in FIGS. 5 to 9 and SEQ ID No. 9; and; partial nucleotide sequences in the vector (pM1317) including the nucleotide sequence of the cDNA coding for shFas(nd29)-hinge are described in FIGS. 10 to 12 and SEQ ID No. 11). The Fas derivatives used in the present invention as described above may be confirmed for their binding activity with the Fas ligand or inhibitory activity for the Fas-mediated apoptosis by an appropriate assay procedure.

The antisense oligonucleotide for the gene or the mRNA of the Fas or the Fas ligand used in the present invention is not limited to particular sequence as long as it inhibits the expression of the Fas or the Fas ligand, and maybe, for example, the antisense oligonucleotide of the Fas ligand disclosed in International Patent Application Publication No. WO 95/13293 (This publication is herein incorporated by reference).

The prophylactic/therapeutic agent of the present invention may be in the form of a pharmaceutical composition or kit such as an injection or an oral medicine wherein the Fas antagonist is combined with at least one pharmaceutical carrier or medium such as sterilized water, physiological saline, a vegetable oil, a mineral oil, a higher alcohol, a higher fatty acid, or a nontoxic organic solvent; and optional additives such as an excipient, a colorant, an emulsifier, a suspending agent, a surfactant, a solubilizer, a nonadsorptive, a stabilizer, a preservative, a humectant, an antioxidative, a buffer, an isotonizing agent, or a pain relieving agent. Preferably, the AIDS-preventing and treating drug of the present invention is parenterally administered either systemically or locally, and rapidly or gradually, for example, by intravenous, intramuscular, intraperitoneal, or subcutaneous injection. The prophylactic/therapeutic agent of the present invention should be administered at an adequate dose determined by taking the conditions and age of the patient as well as the administration route into the consideration. For example, an adequate divided dose may be selected in the range of approximately 0.1 to 100 mg/kg in the case of systemic administration. The prophylactic/therapeutic agent of the present invention, however, is not limited to the administration route and the dose as described above. The prophylactic/therapeutic agent of the present invention may also contain a combination of two or more Fas antagonists, and may be used in combination with another drug.

The prophylactic/therapeutic agent of the present invention may be formulated into a pharmaceutical preparation in a normal process. For example, an injection may be prepared by dissolving the purified Fas antagonist in a medium such as physiological saline or a buffer and optionally supplementing the solution with an additive such as an antiadsorptive. The preparation may also be in the form of a lyophilizate which is to be reconstituted before the use, and may contain any of the excipients that are generally used for facilitating the lyophilization.

The Fas antagonist used in the prophylactic/therapeutic agent of the present invention suppresses injury of the organ or tissue of the host and exhibits the effect of increasing the survival time and the survival rate in the heart ischemic reperfusion model as described in the Examples or in the GVHD model and in particular, in the GVHD model as described in the Examples. The Fas antagonist also exhibits the suppressive effect for the increase of serum creatinine in the renal disease model, and the suppressive effect for the increase of GOT, GPT and the like which are indices of liver damage as well as the effect of increasing the survival rate in endotoxin-induced liver damage model. Accordingly, the prophylactic/therapeutic agent of the present invention administered to a patient suffering from such diseases will exhibit the effect of suppressing the injury and cell death, and in particular, the apoptosis of the cells of the particular organ or the tissue, and hence, the effect of preventing or treating the disease, the effect of alleviating the conditions and pathology associated with the disease, and the effect of suppressing the progress or worsening of the conditions.

In addition, the agent of the present invention has the effect of facilitating the preservation of various organs as demonstrated by in vitro cytotoxicity inhibitory effect as well as the suppression of the tissue damage in heart and renal ischemic reperfusion models.

It should be also noted that the animals used in the Examples using the anti-Fas ligand antibody are rodents (mouse and rat), and therefore, the prophylactic and therapeutic effects are mainly demonstrated by using anti-mouse Fas ligand antibody. The effects similar to those of the Examples are expected for the anti-human Fas ligand antibody and the humanized anti-human Fas ligand antibody when they are administered to human.

The Fas antagonist has prophylactic and therapeutic effects to heart diseases, GVHD, renal diseases, the diseases based on ischemic reperfusion injury, the diseases based on organ damage; effects as an organ preservative; as well as effects of inhibiting cell apoptosis. Therefore, the Fas antagonist used in the present invention and the drug containing such Fas antagonist are quite useful as a prophylactic and therapeutic agent for diseases wherein the Fas-mediated apoptosis is involved. For example, the agent of the present invention is capable of preventing and treating heart diseases, in particular, ischemic heart diseases such as myocardial infarction; myocarditis caused by various factors; cardiomyopathy, and in particular, dilated cardiomyopathy; heart failure; and ischemic reperfusion injury and heart diseases caused by such ischemic reperfusion injury.

The agent of the present invention is capable of preventing and treating GVHD and the conditions and pathology associated with the GVHD. The GVHDs include GVHD after bone marrow transplantation such as incompatible bone marrow transplantation and bone marrow transplantation in congenital immune deficiency; GVHD after organ transplantation; posttransfusional GVHD such as GVHD after blood transfusion of a large amount to a patient of hypoimmunity; and the like. The GVHD is associated with organ or tissue failure based on the GVH reaction, and diarrhea, exhaustion such as weight loss and thinning, exanthem, and liver dysfunction are observed. The GVHD is histologically characterized by such symptoms as disorganization of bone marrow and lymphoid tissue and atrophy of intestinal villi. The agent of the present invention can also be used for prevention and treatment of such conditions and pathology associated with the GVHD.

The agent of the present invention may also be used for direct prevention or treatment of the damages and dysfunctions of various organs in ischemic reperfusion injury found in liver, heart, kidney, lung, spleen, small intestine, large intestine, stomach, pancreas, brain, muscle, skin, and the like, as well as the diseases based on ischemic reperfusion injury such as liver failure, reperfusion arrhythmia, renal failure, necrotizing enterocolitis and the like. In addition, when reperfusion after the ischemia is required in the course of a surgery or transplantation, the agent of the present invention is expected to exhibit a prophylactic or therapeutic effect for the damage of the organ or tissue to improve the posttransplantation acceptance rate and maintain the function of the organ or the tissue. The agent of the present invention is also expected to exhibit an effect of inhibiting the tissue damage and formation or expansion of necrotic infarcted lesion as well as the effect of improving the organ or tissue dysfunction. The agent of the present invention may also be used as an agent for preventing or treating the disease caused by ischemic reperfusion injury after thrombolytic therapy or angioplasty. The agent of the present invention may also be used for the purpose of direct prevention and treatment of the damage and dysfunction of liver or kidney in the diseases based on various organ failures such as liver failure and renal failure, as well as prevention, treatment and alleviation of jaundice, increase in blood GPT, GOT, LDH and the like, fatigue, malaise, hypophagia, consciousness disorder, excitation, coma, ascites, decrease in filtration volume by glomerulus, edema, proteinuria, oliguria, hyperkalemia, metabolic acidosis, increase in blood creatinine and blood urea nitrogen, and the like associated with such diseases. The agent of the present invention can also be used as an organ preservative for transplantation which is used by addition to the preservative fluid used in the transplantation of the tissue or organ or by addition to the perfusate of the organ. Furthermore, the agent of the present invention can be used as an agent for preventing or treating the diseases wherein Fas is involved such as the diseases based on ischemic reperfusion injury as described above. The agent of the present invention can also be used as an agent for preventing or treating MODS associated with SIRS.

The Fas antagonist used in the present invention suppresses not only the damage of acute stage but also the damage of chronic stage in the case of the organ damage caused by endotoxin, in particular, liver damage, endotoxemia or sepsis. Therefore, the Fas antagonist used in the present invention is expected to prevent, treat or alleviate the diseases based on such damages and the pathology associated with such diseases, and therefore, the Fas antagonist has properties quite preferable as a drug.

With regard to the liver, the Fas antagonist used in the present invention is expected exhibit prophylactic, therapeutic, or alleviating effects for liver failure, tissue damage and liver dysfunction in ischemic reperfusion injury caused by decrease or blockage of blood flow (blood supply) in surgery such as transplantation or in shock or circulation failure. With regard to the heart, the Fas antagonist used in the present invention is expected to exhibit prophylactic, therapeutic, or alleviating effects for irreversible cell death and lethal arrhythmia caused by overload of intracellular calcium ion as a result of reperfusion after recanalization, percutaneous transluminal coronary recanalization (PTCR) or percutaneous transluminal coronary angioplasty (PTCA) for myocardial infarction. With regard to the kidney, the Fas antagonist used in the present invention is expected to exhibit prophylactic, therapeutic, or alleviating effects for renal ischemia after surgery or kidney transplantation, renal ischemic reperfusion injury, diseases based on such ischemia or ischemic reperfusion injury, renal failure, the diseases causing such renal failure, and damages of cells inherent to renal glomeruli (endothelial cells, epithelial cells, mesangial cells), mesangial matrix, extracellular matrix of basal membrane or epithelial cells of tubule.

EXAMPLES

Next, the present invention is described in further detail by referring to Examples which by no means limit the scope of the present invention.

Example 1.

Production of shFas(nd29)-Fc and shFas (nd29)-hinge (1) Production and Cultivation of Transformants Transformants COS-1/pM1304, COS-1/pM1317, and COS-1/pBF-Fc1 were prepared by the procedure as described below by using pM1304, pM1317, and pBF-Fc1 (the expression plasmid for the chimeric protein (often designated as hFas-Fc) of the extracellular domain of the human Fas antigen and Fc region of human IgG1) described in Example 1 of International Patent Application Publication No. WO 95/13293. 100 µg of the plasmid DNA was respectively dissolved in 500 µl of 10 mM Tris-HCl (pH 7.4)/1 mM ethylenediaminetetraacetatic acid solution (hereinafter abbreviated as TE buffer). The solutions were respectively supplemented with 0.2 mg/ml DEAE-dextran and 125 ml of D-MEM (Nissui Seiyaku) supplemented with 50 mM Tris HCl (pH 7.4) to prepare DNA-DEAE dextran mixed solution. The DNA-DEAE dextran mixed solutions were respectively added to monolayer cultures of COS-1 cells which had been incubated to semiconfluency in 1700 cm² roller bottles (manufactured by Corning Inc.), and further incubated at 37° C. to obtain the transformants COS-1/pM1304, COS-1/pM1317, and COS-1/pBF-Fc1. After 4 hours, the DNA-DEAE dextran mixed solution was substituted with D-MEM culture medium supplemented with 10% bovine fetal serum (manufactured by Lifetech Oriental K.K.), and incubation was continued for 24 hours. The medium was further substituted with phenol red free D-MEM (FBS, BSA-free), and the incubation was continued for another 72 hours. The culture supernatant was then harvested.

(2) Purification of shFas(nd29)-Fc (i) Affinity chromatography

After precipitating 1 liter of the culture supernatant of COS-1/pM1304 with ammonium sulfate (70% saturation), the precipitate was suspended in phosphate buffer saline (PBS) and dialyzed against PBS. To AFFI PREP Protein A Preparative Cartridge Column (Protein A affinity chromatography matrix, manufactured by Biorad Inc.; 7.3 ml) was applied 57 ml of the resulting suspension, and the shFas (nd29)-Fc eluted was collected, and concentrated by ultrafiltration using FILTRON OMEGA CELL (polyetheusulfone ultracentrifugation membrane, manufactured by Fuji Filter K.K.; fractionating molecular weight: 30 kD). The concentrate was dialyzed against 0.9% NaCl to obtain the purified shFas(nd29)-Fc. hFas-Fc was purified in a similar manner. The amount of the protein in each specimen was measured by Lowry's method using bovine serum albumin for the standard.

The resulting purified shFas(nd29)-Fc was electrophoresed on a 5 to 20% gradient polyacrylamide gel containing 0.1% SDS, and stained with 2D-SILVER STAIN-II "Daiichi" (silver staining kit manufactured by Daiichi Kagakuyakuhin K.K.) to detect the bands. The purified shFas(nd29)-Fc was detected under non-reduced conditions as a substantially single band of about 85 kD corresponding to the dimer, and under reduced conditions as a substantially single band of about 43 kD corresponding to the monomer.

The resulting shFas(nd29)-Fc was applied to VYDAC C4 column (4.6 mm diam.×25 cm, synthetic-silsica-based reversed-phase chromatography column manufactured by Cypress Inc.) preliminarily equilibrated with 0.05% trifluoroacetic acid, and the column was washed with 0.05% trifluoroacetic acid. After the washing, the column was eluted at linear concentration gradient method at a flow rate of 1 ml/minute using 0.05% trifluoroacetic acid/0 to 100% acetonitrile.

The elution fraction of the main peak was lyophilized, and dissolved in 70% formic acid for use as a sample, and the sample was analyzed for its N terminal amino acid sequence by Model 477A Protein Sequencing System—120A PTH Analyzer (manufactured by Perkin Elmer Inc.). In the analysis, PTH amino acid was detected by measuring absorbance at 270 nm in the ultraviolet region, and comparing the data by using the retention time of the standard PTH amino acid (manufactured by Perkin Elmer Inc.) which had been preliminarily separated by the same procedure. It was then found that the sample has the N terminal sequence of the human Fas antigen from which 29 N terminal amino acid residues had been deleted (Thr Gln Asn Leu Glu Gly Leu His His Asp).

(3) Purification of shFas(nd29)-hinge

Anti-Fas monoclonal antibody (4B4-B3) prepared by a known method (Kohler and Milstein, Nature, vol. 256, page 495, 1975) using the splenocyte of the mouse immunized with the human Fas antigen and mouse myeloma cell was mixed with formyl-cellulofine (manufactured by Seikagaku Kogyo K.K.) to produce an antibody affinity column by the standard method.

10 liters of the culture supernatant of COS-1/pM1317 was concentrated to 1.5 liters by ultrafiltration using FILTRON MINI kit (fractionating molecular weight: 10 kD; manufactured by Fuji Filter K.K.). The concentrate was supplemented with 1M Tris-HCl (pH 9.0) to adjust the pH to 8.0, and the solution was applied to an affinity column having the anti-Fas antigen monoclonal antibody immobilized thereto which had been equilibrated with 50 mM Tris-HCl (pH 8.0) containing 1M NaCl. The column was washed with 320 ml of 50 mM Tris-HCl (pH 8.0) containing 1M NaCl, and shFas(nd29)-hinge was eluted with 0.1M glycine-HCl (pH 2.5). The fractions containing the shFas(nd29)-hinge were pooled, and concentrated by using FILTRON OMEGA CELL (fractionating molecular weight: 10 kD; manufactured by Fuji Filter K.K.). The concentrate was dialyzed against 0.9% NaCl to obtain the purified shFas(nd29)-hinge.

The resulting purified shFas(nd29)-hinge was electrophoresed on a 5 to 20% gradient polyacrylamide gel containing 0.1% SDS, and stained with 2D-SILVER STAIN-II "Daiichi" (manufactured by Daiichi Kagakuyakuhin K.K.) to detect the bands. The purified shFas(nd29)-Fc was detected under non-reduced conditions as two bands at a molecular weight of about 43 kD and about 27 kD, and under reduced conditions as two bands of about 23 kD and 27 kD.

The resulting shFas(nd29)-hinge was analyzed for its N terminal amino acid sequence by repeating the procedure as described above. It was then found that the shFas (nd29)-hinge has the N terminal sequence of the human Fas antigen from which 29 N terminal amino acid residues had been deleted.

(4) Comparison of the Apoptosis Inhibitory Activity Between shFas(nd29)-Fc and shFas(nd29)-hinge The shFas(nd29)-Fc and the hFas-Fc were respectively measured for their activity to inhibit the cytotoxic activity of 1A12 cell and FLm14 cell to WC8 cell and W4 cell for use as an index. 1A12 cell is a transformant of mouse WR19L cell that had been transformed for the expression of the human Fas ligand, and FLm14 cell is a transformant of mouse FDC-P1 cell that had been transformed for the expression of the mouse Fas ligand. WC8 cell and W4 cell are transformants of mouse WR19L that had been transformed for the expression of the human Fas antigen and mouse Fas antigen, respectively. The WR19L cell is a cell which scarcely expresses the mouse Fas antigen and which is sensitive to cytotoxic action of TNF. The measurement of the cytotoxic activity was conducted in accordance with the method of Rouvier, E. et al. (Journal of Exp. Med., vol. 177, pages 195–200, 1993). First, the 1A12 cell and the FLm14 cell were respectively washed with RPMI 1640 supplemented with 10% inactivated FBS for use as effecter cells. In the meanwhile, $1\times10^6$ WC8 cells and W4 cells were respectively incubated at 37° C. for 2 hours in 100 μl of RPMI 1640 supplemented with 10% inactivated FBS together with 20 μCi of [$^{51}$Cr] sodium chromate (manufactured by NEN Inc.). After washing the cells with the RPMI 1640 supplemented with 10% inactivated FBS, the cells were used for the target cells. $1\times10^4$ 1A12 cells or $1\times10^5$ FLm14 cells and $1\times10^4$ target cells were mixed with the shFas (nd29)-Fc and the hFas-Fc of various concentrations in the wells of a round bottom microtiter plate, such that the total amount of the liquid was 100 μl. The plate was centrifuged at 800 rpm for 2 minutes, incubated at 37° C. for 4 hours, and further centrifuged at 1,200 rpm for 5 minutes. An aliquot of 50 μl collected from each well was measured for its Radioactivity with a γ counter to calculate the percentage of specific cell lysis. Spontaneous release of $^{51}$Cr was determined by incubating only the target cells in the culture medium. The maximum release was determined by adding Triton X-100 to the target cells to 0.1%.

The shFas (nd29)-Fc and the hFas-Fc were compared for their activity to inhibit the cytotoxicity by comparing the suppression when the 1A12 cells were used for the effector cells and the WC 8 cells were used for the target cells and when the FLm14 cells were used for the effector cells and the W4 cells were used for the target cells, and it was then found that the shFas(nd29)-Fc had a cytotoxicity-inhibitory activity 3 to 10 times higher than that of the hFas-Fc.

When evaluated in a similar procedure, shFas (nd29)-hinge had a cytotoxicity-inhibitory activity 3 to 10 times higher than that of the hFas-Fc.

Example 2.

Effects of Fas Antagonist in Heart Disease Model (1) Production of Heart Ischemic Reperfusion Model Male Wistar rats of 320 to 450 g (Charles River Japan K.K.) were anesthetized by intraperitoneal administration of 60 mg/kg of Nembutal (manufactured by Dainippon Pharmaceutical Co., Ltd.). After fixing the rat on a temperature-maintaining plate (IKEDA SCIENTIFIC CO. LTD.) maintained at 35° C. in supine position, trachea was incised to connect a respirator (manufactured by Shinano Seisakusho, SN-480-7), and chest was then dissected at left side, fourth intercostal space to expose the heart, and 2 to 3 mm upstream from the origin of left coronary artery was ligated by a single bowknot with threaded suture needle (opthamologic lightly curved needle, manufactured by Natsume Seisakusho K.K.). The ligation was undone after 20 minutes by untieing the single bowknot, and the artery was reperfused for 3 hours. The artery was ligated again to determine the region of the ischemia, and physiological saline containing 1% Evans blue was injected from left femoral vein. The heart was then extirpated, frozen with liquid nitrogen, cut into five pieces with a razor (manufactured by Feather Safety Razor K.K.), and stained in physiological saline containing 1% TTC (2,3,5-triphenyltetrazooium chloride, manufactured by Wako Pure Chemical Industries, Ltd.) at 37° C. for 20 minutes. The sections were stored in 10% neutral buffered formalin for the subsequent analysis. Blood was collected from cervical vein at 1 hour and 3 hours after the reperfusion to measure creatine kinase (CPK) in plasma.

(2) Administration of Human Fas-Fc

The human Fas-Fc (hFas-Fc) used was the one prepared according to the method described in Example 1 of International Patent Application Publication No. WO 95/13293. The hFas-Fc was diluted with physiological saline supplemented with 0.1% human serum albumin (manufactured by Research Institute of Chemotherapy and Serotherapy (Foundation)), and administered at a dose of 1 mg/10 ml/kg from the right femoral vein immediately after the start of the reperfusion. The group of five rats administered with 1 mg/kg of hFas-Fc and the control group of eight rats were used.

(3) Measurement of Non-ischemic, Ischemic and Necrotic Regions

The proportion of non-ischemic region (the region positive for Evans blue and positive for TTC), ischemic region (the region negative for Evans blue and positive for TTC) and necrotic region (the region negative for Evans blue and negative for TTC) in the sections were calculated as described below. The images obtained with a stereoscopic microscope (SHZ10, manufactured by Olympus Optical Co., Ltd.) from both sides (upper side, lower side) of the heart sections were input in an image analyzer software (Image Command 5098, product of Olympus Optical Co., Ltd.), the non-ischemic, ischemic and necrotic regions were defined on the monitor, and each of the thus defined non-ischemic, ischemic and necrotic regions were printed out. The area of each region was measured by digital planimeter (manufactured by Uchida Yoko Co., Ltd.). Next, wet weight of each region was calculated by the following formula. The wet weight of each region=$0.5 \times (A+B) \times$ wet weight of the section, wherein A and B are respectively the area proportion of the regions on the upper and lower side of the section.

(4) Calculation of the Proportion (%) of Non-ischemic, Ischemic and Necrotic Regions in the Heart Specimen The sum of the wet weight of the non-ischemic region of each section was designated as the total wet weight of the non-ischemic regions. The proportion (%) of the total wet weight of the non-ischemic regions in the sum of the wet weight of each section (total wet weight of the heart sample) was designated as the proportion (%) of the non-ischemic region in the heart sample. Total wet weight and proportion (%) in the heart sample were calculated in a similar manner for the ischemic region and the necrotic region.

(5) Measurement of Creatine Kinase (CPK) in Plasma

The value of creatine kinase (CPK) in plasma was measured by using CPK TESTWAKO and autoanalyzer (COBAS FARA, manufactured by Roche).

(6) Results

Figure 14:
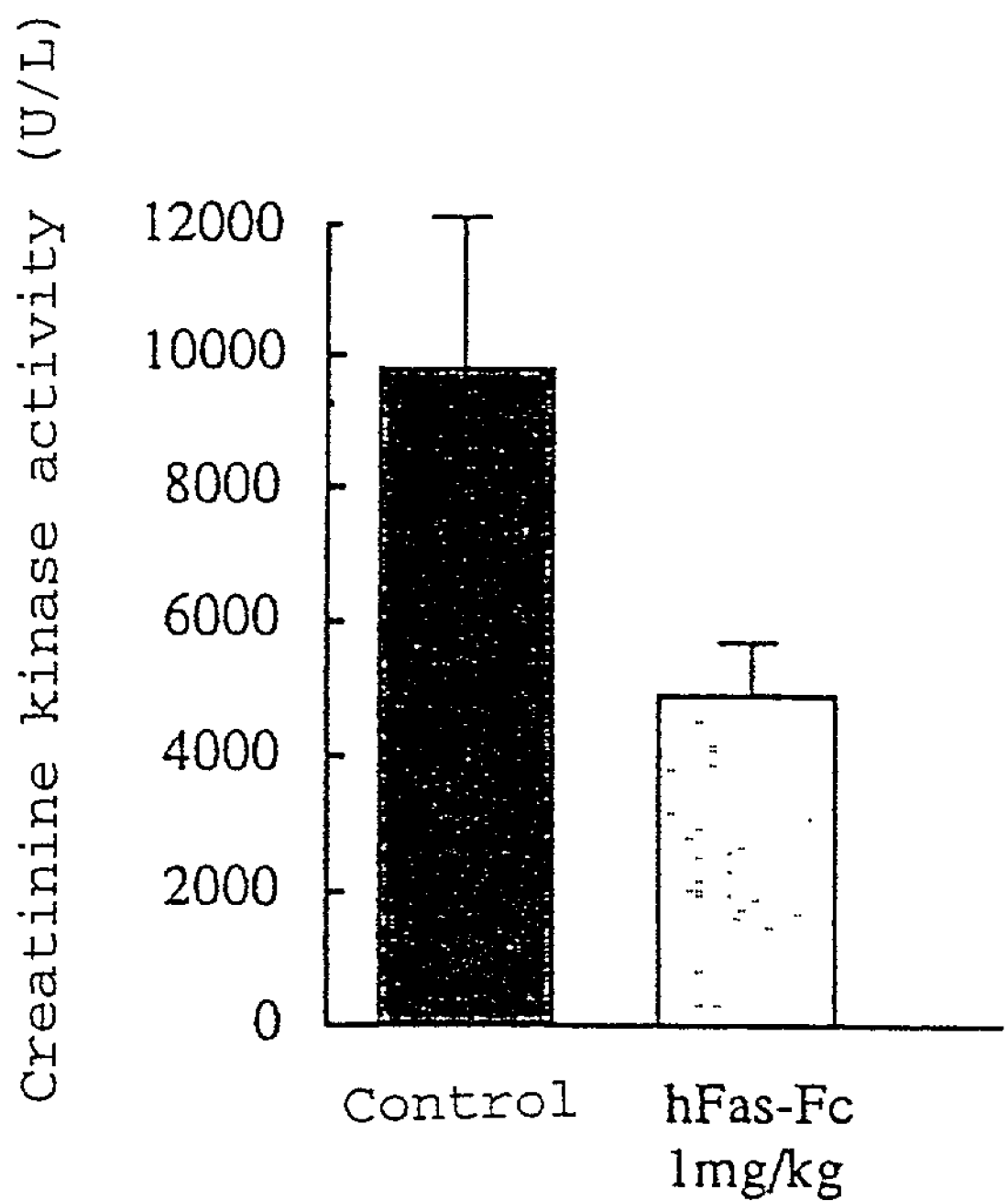
FIG. 14 is a view showing the suppressive effect of the Fas derivative (hFas-Fc) for increase of plasma CPK value at 3 hours after the reperfusion in an experimental rat model of heart ischemic reperfusion injury.

The proportion (%) of the necrotic region to the ischemic region in the hFas-Fc treated group was lower than that of the control group (FIG. 13). The creatine kinase (CPK) activity value of the hFas-Fc treated group was lower than that of the control group (FIG. 14).

Example 3.

Toxicity Test of hFas-Fc (1) Method

Male ICR mice of 7 week old (Nihon SLC K.K.) were intraperitoneally administered with 2.5 mg/kg of hFas-Fc every day for 3 days. The mice were measured everyday for the body weight from one day before the start of the administration to one day after the finish of the administration to evaluate the effects of the hFas-Fc administration on the body weight. The mice were subjected to autopsy one day after the finish of the administration, and main organs were inspected with naked eye and splenocytes were counted to examine the effects of the hFas-Fc administration.

(2) Results

The intraperitoneal daily administration of the hFas-Fc at a dose of 2.5 mg/kg for 3 days gave no effects on the body weight and the splenocyte count. No effects of the administration of the hFas-Fc were observed in autopsy.

Example 4

Effects of the Fas Antagonist in Mouse GVHD Model (1) Myelosuppression in the Host Mouse Male BDF1 mice of 6 week old (Charles River Japan K.K.) were used for the host mice. The host mice were intraperitoneally administered with 450 mg/kg of cyclohosphamide (Shionogi & Co., Ltd., Endoxan) to induce myelosuppression.

(2) Preparation of the Splenic Lymphocytes from the Donor Mouse, and Transplantation the Splenic Lymphocytes to the Host Mouse A 7 week old male C57BL/6mouse (Charles River Japan K.K.) was used for the donor mouse. Spleen from the donor mouse was disintegrated in Hank's solution (manufacture by Nissui Seiyaku K.K.) with forceps, centrifuged, and suspended in 0.017M Tris-0.747% ammonium chloride solution for selective hemolysis of erythrocytes. The residual cells washed with Hank's solution were used as splenic lymphocytes from the donor mouse, and $3 \times 10^7$ cells/mouse were transplanted to the host mice from their tail vein on the next day of the cyclophosphamide administration as described above.

(3) Evaluation of the Effects of hFas-Fc

Figure 15:
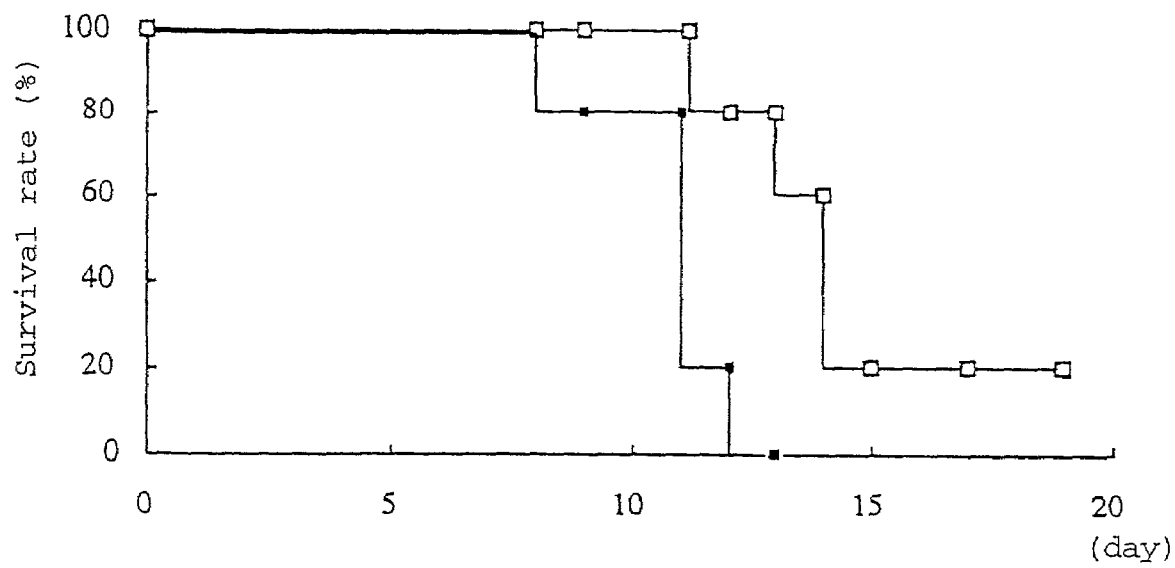
FIG. 15 is a view showing the effect of the human Fas-Fc in extending the survival time in mouse GVHD model. Blank square (□) represents the survival rate of the group administered with 10 mg/kg of hFas-Fc, and solid square (■) represents the survival rate of the control group.

Effects of the hFas-Fc administration on the survival time was evaluated by administering 1, 3 or 10 mg/kg of hFas-Fc from the tail vein from the next day of the transplantation of the splenic lymphocytes from the donor mouse. It should be noted that the control group was administered with the physiological saline supplemented with 0.1% human serum albumin (manufactured by Research Institute of Chemotherapy and Serotherapy (Foundation)), which was the diluent used for the hFas-Fc. n was 5 for each group. The survival time elongating effect was observed for the group treated with 10 mg/kg of hFas-Fc in comparison with the control group (FIG. 15). This group also exhibited less weight loss.

Example 5.

Production of shFas(nd29)-Fc-producing CHO Cell (CHO(pM1304)72-105-55)

(1) Production of shFas(nd29)-Fc Transformant

16 µg of plasmid pM1304 was dissolved in 5.5 µl of 10 mM Tris-HCl (pH 7.4)/1 mM ethylenediaminetetraacetic acid solution. F-12 Nutrient Mixture (Ham) medium was added to this solution (3:1 (w/w) liposome formulation of DOSPA and DOPE, manufactured by GIBCO BRL Inc., hereinafter abbreviated as HamF12 medium) to a total volume of 800 µl to prepare solution A. Ham F12 medium was added to 96 µl of Lipofect AMINE reagent (manufactured by GIBCO BRL Inc.) to a total volume of 800 µl to prepare solution B. The solution A and the solution B were mixed, and the mixture was incubated at room temperature for 30 minutes and supplemented with 6.4 ml of HamF12 medium to prepare DNA-Lipofect AMINE mixed solution. $1.2 \times 10^6$ CHO DXB11 cells which had been inoculated in petri dish of 10 cm diam. (manufactured by Corning) on the previous day were washed with HamF12 medium, and supplemented with 8 ml of the DNA-Lipofect AMINE mixed solution. The cells were incubated in the presence of 5% $CO_2$/95% air at 37° C. for 7.5 hours, the DNA-Lipofect AMINE mixed solution was removed and substituted with HamF12 medium supplemented with 10% inactivated bovine fetal serum (manufactured by JRH BIOSCIENCES Inc.), and the culture was continued for another 24 hours. The medium was again substituted with HamF12 medium supplemented with 10% inactivated bovine fetal serum, and the cultivation was continued for 24 hours. The cells were reinoculated at $10^3$, $10^4$, and $10^5$ cells/10 ml HamF12 medium supplemented with 10% inactivated bovine fetal serum/petri dish of 10 cm diam. 2 days after the reinoculation, the medium was substituted with minimum essential medium αmedium without ribonucleotides and deoxyribonucleotides (manufactured by GIBCO BRL, hereinafter abbreviated as MEMα(-) supplemented with 10% inactivated and dialyzed bovine fetal serum to initiate the selection of the cells having DHFR gene incorporated therein. The medium was substituted at every 3 or 4 days with new MEMα(-) supplemented with 10% inactivated and dialyzed bovine fetal serum, and colonies of DHFR positive cells started to form in about 2 weeks. The DHFR positive cells expressing shFas(nd29)-Fc were then cloned in accordance with the method of Nobuhara et al. (Jikken Igaku (Experimental Medicine), vol. 5, No. 11, 1987, pages 1108–1112). More illustratively, about 100 single colonies were cloned by using penicillin cup, and subcloned on 48 well plates (manufactured by NUNC). The cells were incubated by substituting the medium at every 3 or 4 days with new MEMα(-) supplemented with 10% inactivated and dialyzed bovine fetal serum, and the cultivation was continued at a greater scale when the well became confluent. When the cells proliferated to the extent that the wells of 6 well plates (manufactured by NUNC) were confluent, cell number was adjusted by inoculating at $2.5 \times 10^5$ cells/500 µl MEMα(-) supplemented with 10% inactivated and dialyzed bovine fetal serum/24 well plate (manufactured by NUNC), and the culture supernatant was harvested after 2 to 3 days. The content of shFas(nd29)-Fc in the supernatant was measured by EIA to select the cell line of high expression (CHO (pM1304)72).

(2) Production of the Cell Line Expressing shFas (nd29)-Fc at a High Level (CHO(pM1304)72-105-55) by Gene Amplification Gene amplification with methotrexate (MTX) was conducted in accordance with the method of Nobuhara et al. (Jikken Igaku (Experimental Medicine), vol. 5, No. 11, 1987, pages 1108–1112) to produce the cell line of high shFas (nd29)-Fc expression. More illustratively, the CHO (pM1304) 72 cells were inoculated at $10^3$, $10^4$, and $10^5$ cells/10 ml MEMα(-) medium supplemented with 10% inactivated bovine fetal serum/petri dish of 10 cm diam., and the medium was substituted with MEMα(-) supplemented with 10% inactivated and dialyzed bovine fetal serum containing 5 nM MTX (manufactured by Lederle) to initiate the gene amplification. The medium was substituted at every 3 or 4 days with new MEMα(-) supplemented with 10% inactivated and dialyzed bovine fetus serum containing 5 nM MTX, and colonies of MTX resistant cells started to form in about 2 weeks. The procedure adapted in producing the CHO(pM1304)72 cells was repeated to produce a cell line of high shFas (nd29)-Fc expression which is resistant to 5 nM of MTX (CHO(pM1304)72-105). Similar procedure was also repeated to produce a cell line of high shFas(nd29)-Fc expression which is resistant to 50 nM of MTX (CHO (pM1304)72-105-55).

Example 6.

Production of shFas (nd29)-Fc by using the CHO cell, and Its Purification (1) Culture of the shFas(nd29)-Fc-producing CHO Cell $2.3 \times 10^4$ cells/cm$^2$ of CHO(pM1304)72-105-55 produced in Example 5 were inoculated in Cell Factory (manufactured by Nunc) having a culture area of 6000 cm$^2$ by using IBL Media I (manufactured by Meneki Seibutsu Kenkyujo K.K.) containing 50 mM MTX for the growth medium in the presence of 5% $CO_2$/95% air at 37° C. for 6 days. After confirming confluency, the medium was substituted with IBL media I from which insulin and transferin had been removed (productive medium). The cells were cultured in the presence of 5% $CO_2$/95% air at 37° C. for another 4 days, and the supernatant was harvested. The cells after the collection of the supernatant was supplemented with the productive medium, and the cells were cultured for another 4 days for second harvest of the supernatant.

(2) Purification of shFas(nd29)-Fc from the Culture Supernatant of the CHO Cell

The procedure of Example 1(2) was repeated for purification of shFas (nd29)-Fc from the culture supernatant as described above by using protein A chromatography.

Example 7.

Toxicity Test of shFas(nd29)-Fc

In order to examine the toxicity of shFas(nd29)-Fc, male BDF1 mice of 6 week old (Charles River Japan K.K.) were administered with shFas(nd29)-Fc at a dose of 10 or 30 mg/kg once in every two days for 12 days, namely, for 7 times in total from the tail vein to examine the effects. The experiment was conducted by using three groups, namely, the control group, the group administered with 10 mg/kg of shFas(nd29)-Fc, and the group administered with 30 mg/kg of shFas(nd29)-Fc, and n was 3 for each group. It should be noted that, in order to administer the same amount, namely, 30 mg/kg of protein, the control group was administered with 30 mg/kg of human serum albumin; the group of 10 mg/kg shFas(nd29)-Fc administration was administered with 10 mg/kg of shFas(nd29)-Fc and 20 mg/kg of human serum albumin; and the group of 30 mg/kg shFas (nd29)-Fc administration was administered with 30 mg/kg of shFas (nd29)-Fc. The body weight was measured once in every two days from the day of the start of the administration. Blood was collected from orbital vein on 14th day from the start of the administration, and after counting blood cells, plasma was prepared to measure GOT, GPT and creatinine. The mice were subjected to autopsy after the blood collection, and main organs (lung, heart, liver, kidney, spleen, and intestine) were examined with naked eye if there were any alteration. The blood cells were counted by using an automatic blood cell counter K-2000 of Sysmex Inc. GOT, GPT and creatinine were measured by using an autoanalyzer (COBAS FARA, manufactured by Roche).

It was then found out that administration to the mouse of 10 or 30 mg/kg of shFas(nd29)-Fc once in every two days for 12 days, namely, for 7 times in total gave no significant effects in weight increase, blood cell count, liver (GOT, GPT), kidney (creatinine), and other main organs (observation with naked eye).

Example 8.

Effects of the Fas Antagonist in Endotoxin-induced Liver Damage Model (1) Liver Damage Inhibitory Effect of the shFas(nd29)-Fc in Mouse C57BL/6Cr Slc mice (male, 9 week old, Japan SLC K.K.) were used for the test animal by forming 3 groups of animals each comprising 5 mice. The mice were administered from their tail vein with 0.2 ml of physiological saline having dissolved therein heat-killed *Propionibacterium acness* (*P. acness*) (RIBI IMMUNOCHEM RESEARCH, INC.) to a concentration of 5.0 mg/ml. 8 days after the administration, the mice were administered from their tail vein with shFas (nd29)-Fc prepared in Example 1 which had been diluted with a diluent (physiological saline containing 0.1% human serum albumin) at a dose of 0.3 mg/8 ml/kg or 1 mg/8 ml/kg. The control group was administered with the diluent. After 5 minutes, the mice were intraperitoneally administered with 0.2 ml of a solution of lipopolysaccharide (manufactured by Sigma) adjusted to a concentration of 5 µg/ml with physiological saline. 75 µl of blood was collected from orbital at 8 and 24 hours after the administration of the lipopolysaccharide. The blood collected was mixed with 8.3 µl of 3.8% aqueous solution of sodium citrate, and centrifuged at 3000 rpm for 10 minutes. After the centrifugation, the resulting plasma was frozen by liquid nitrogen and stored at −30° C. until the use. GOT and GPT were measured with GOT-FA TestWako (manufactured by Wako Pure Chemical Industries, Ltd.), GPT-FA TestWako (manufactured by Wako Pure Chemical Industries, Ltd.), and an autoanalizer (Roche, COBAS FARA). It was then found that the GOT and GPT values in the group administered with 1 mg/8 ml/kg of shFas(nd29)-Fc were lower than the values of the control group to demonstrate the liver damage inhibitory effect.

(2) Liver Damage Inhibitory Effect of the shFas(nd29)-hinge in Mouse

The procedure as described above was repeated by using C57BL/6Cr Slc mice (male, 9 week old, Japan SLC K.K.) for the test animal, and by forming 3 groups of animals each comprising 5 mice. It was then found that the GOT and GPT values in the group administered with shFas (nd29)-hinge were lower than the values of the control group to demonstrate the liver damage inhibitory effect.

Example 9.

Effects of the Anti-human FasL Antibody in Endotoxin-induced Liver Damage Model (1) Production of Liver Damage Model Mouse Male, 5 week old BALB/c mice (Japan SLC K.K.) were used. The mice were administered from their tail vein with 0.2 ml of physiological saline containing 5.0 mg/ml of heat-killed Propionibacterium acness (*P. acness*) (RIBI IMMUNOCHEM RESEARCH, INC.). 10 days after the administration, the mice were administered from their tail vein with 0.2 ml of 50 µg/ml dilution of the extracellular domain of the human Fas ligand in physiological saline supplemented with 0.1% human serum albumin to prepare liver damage model mice. It should be noted that the extracellular domain of the human Fas ligand was obtained by transforming Pichia yeast (*Pichia pastoris*) GS 115 strain (manufactured by Invitrogen) with an expression plasmid which is a plasmid for Pichia yeast pPIC9 (manufactured by Invitrogen) having the DNA coding for the extracellular domain of the human Fas ligand incorporated therein; obtaining the culture supernatant of the transformant; and purifying the culture supernatant by means of salt precipitation with 80% saturation ammonium sulfate, protein A-Cellulofine affinity column having hFas-Fc bound thereto, Mono S (manufactured by Pharmacia) column, or other purification means (Tanaka, M. et al., Nature Medicine, vol. 2, pages 317–322, 1996). The one prepared by the procedure described in Example 18 of International Patent Application Publication No. WO 95/13293 is similarly usable.

(2) Mortality Suppressive Effect of the Anti-human Fas Ligand Antibody

Figure 16:
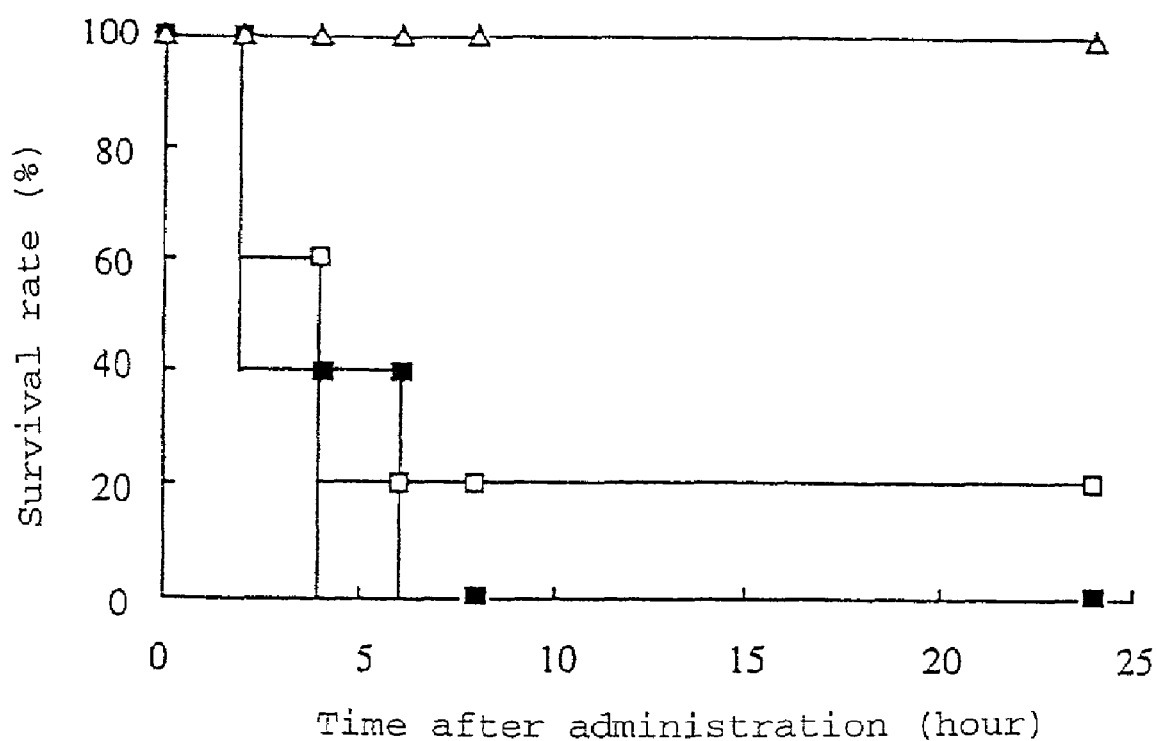
FIG. 16 is a view showing the suppressive effect of the anti-human Fas ligand antibody for the mortality in mouse liver damage model. Blank square (□) represents the survival rate of the group administered with 0.4 mg/kg of F919-9-18, blank triangle (∆) represents the survival rate of the group administered with 1.2 mg/kg of F919-9-18, and solid square (■) represents the survival rate of the control group.

Mouse anti-human Fas ligand monoclonal antibody F919-9-18 produced by the hybridoma F919-9-18 with the Accession No. of FERM BP-5535 as described above was used. The group administered with the mouse anti-human Fas ligand monoclonal antibody F919-9-18 was administered from the tail vein with 0.4 mg/kg or 1.2 mg/kg of F919-9-18 at 5 minutes before the administration of the extracellular domain of the human Fas ligand. The control group was administered with the physiological saline supplemented with 0.1% human serum albumin which was the diluent for the anti-human Fas ligand antibody. n was 5 for each group. It was then revealed that in the control group, all mice were dead before 8 hours after the administration of the anti-human Fas ligand antibody while the survival rate at 24 hours after the administration of the group administered with 0.4 mg/kg of the anti-human Fas ligand antibody was 20%, and the survival rate at 24 hours after the administration of the group administered with 1.2 mg/kg of the anti-human Fas ligand antibody was 100% (FIG. 16).

Example 10.

Production of Anti-mouse Fas Ligand Antibody and its Purification (1) Production of Anti-mouse Fas Ligand Antibody A plasmid containing human elongation factor (EF) promoter, and in its downstream, the gene coding for the chimeric protein prepared by fusing the extracellular domain of mouse Fas ligand from soluble mouse Fas ligand WX2 (J. Immunology, vol. 157, pages 3918–3924, 1996) and the intracellular domain, the transmembrane domain, and a part of the extracellular domain (from N terminal to 78th amino acid) of mouse CD40 ligand was prepared (Mizushima-Nagata, Nucleic Acids Research, vol. 18, page 5322, 1990). The plasmid was transfected in WR19L cell to obtain a recombinant cell W40LFL expressing the mouse Fas ligand on its cell membrane for use as the antigen to be administered. Armenian hamsters were used for the animals to be immunized. The Armenian hamsters were subcutaneously administered with $1 \times 10^7$ W40LFL mixed with Freund complete adjuvant, and a month later, subcutaneously administered with $2 \times 10^7$ W40LFL suspended in PBS, and in another a month later, administered with $5 \times 10^6$ W40LFL suspended in PBS from the foot pad. 3 days after the administration, lymph node cells were collected and fused with mouse myeloma cell P3-X63-Ag8-U1 (P3-U1). After selecting the hybridoma by HAT medium (hypoxanthine-aminopterin-thymidine), hybridomas FLIM4 (#4-2), FLIM23 (#23-2), FLIM58(#58-11) whose supernatants had neutralizing activity for cytotoxicity of mouse Fas ligand were obtained from the survived hybridomas.

(2) Production of FLIM58 (#58-11) and Its Purification

Hybridoma (#58-11) was cultured in serum-free medium Hybridoma-SFM (GIBCO BRL), and the culture supernatant was purified by protein A column (PROSEP-A, Bioprocessing) to obtain purified antibody FLIM58 (#58-11). Concentration of the protein was calculated from absorbance at 280 nm.

Example 11.

Neutralizing Activity of the Anti-mouse Fas Ligand Antibody #58-11 for the Mouse and Rat Fas Ligands Neutralizing activity for anti-mouse Fas ligand antibody #58-11 was evaluated by an assay using release of $^{51}Cr$ for the index by repeating the procedure described in Example of International Patent Application Publication No. WO 95/13293.

(1) Preparation of Effector Cells

Splenocytes from male, 7 week old ICR mice (Charles River Japan K.K.) and male, 11 week-old Wistar rats (Charles River Japan K.K.) were prepared by repeating the procedure of Example 4. The resulting splenocytes were adjusted to a concentration of $2 \times 10^6$ cells/ml, and incubated overnight at 37° C. in PRMI 1640 medium (GIBCO BRL) supplemented with 40 U/ml of recombinant human IL-2 (Boehringer Mannheim) and 10% inactivated FBS (JRH Bioscience) in the presence of 5% $CO_2$ gas. 100 nM conkanamycin A (Wako Pure Chemical Industries, Ltd.) was added and the culture was incubated for 1 hour, and 10 ng/ml PMA (Sigma) and 500 ng/ml ionocycin (CALBIOCHEM) were added and the culture was incubated for another 2 hours. The cells were collected, washed with the PRMI 1640 medium supplemented with 10% inactivated FBS, and suspended in the PRMI 1640 medium supplemented with 10% inactivated FBS to $2.5 \times 10^7$ cells/ml.

(2) Preparation of Target Cells

The preparation of the target cells was conducted by a procedure similar to the procedure described in International Patent Application Publication No. WO 95/13293. More illustratively, a mouse Fas-expressing W4 cell was used for the target cell, and $10^6$ W4 cells were incubated in PRMI 1640 medium supplemented with 20 μCi of $^{51}Cr$ sodium chromate (NEN) at 37° C. in the presence of 5% $CO_2$ gas for 2 hours for $^{51}Cr$ labeling.

(3) Neutralizing Activity of the Anti-mouse Fas Ligand Antibody #58-11 for the Mouse and Rat Fas Ligands Anti-mouse Fas ligand antibody #58-11 of various concentration were added to $1 \times 10^6$ activated mouse and rat splenocytes as described above, respectively, and the cells were incubated at 37° C. for 30 minutes in the presence of 5% $CO_2$ gas. To the cultures were then added $1 \times 10^4$ W4 cells labeled with $^{51}Cr$ as described above, and after the centrifugation at 800 rpm for 2 minutes, the cells were incubated at 37° C. for 4 hours in the presence of 5% $CO_2$ gas. The supernatants were measured for the amount of $^{51}Cr$ after the centrifugation at 1200 rpm for 5 minutes to evaluate the effect of the anti-mouse Fas ligand antibody #58-11. In addition, in order to confirm that the cytotoxic activity of the activated mouse and rat splenocytes as described above is the cytotoxic activity by the FasL, shFas(nd29)-Fc which is the Fas derivative described in International Patent Application No. PCT/JP97/10502 was added in the same manner as the case of the anti-mouse Fas ligand antibody #58-11 as a positive control of the assay. The thus obtained results were analyzed by a procedure similar to the assay procedure described in International Patent Application Publication No. WO 95/13293 using release of $^{51}Cr$ for the index. It was then demonstrated that the shFas(nd29)-Fc used as the positive control inhibits the cytotoxic activity of the activated mouse and rat splenocytes in a dose dependent manner at a concentration in the range of 0.3 μg/ml to 3 μg/ml, and that the activated mouse and rat splenocytes used exhibit FasL dependent cytotoxicity. It was also demonstrated that the anti-mouse Fas ligand antibody #58-11 inhibits the cytotoxic activity of the activated mouse and rat splenocytes in a dose dependent manner at a concentration in the range of 0.3 μg/ml to 3 μg/ml as in the case of the shFas(nd29)-Fc. As described above, the anti-mouse Fas ligand antibody #58-11 inhibited the mouse and the rat Fas ligands.

Example 12.

Toxicity Test of the Anti-mouse Fas Ligand Antibody #58-11

(1) Method

Male, 8 week old DBA/1J mice and C3H/He mice (Charles River Japan K.K.) were used. The mice were administered from their tail vein with the anti-mouse Fas ligand antibody #58-11 at a dose of 100 mg/30 ml/kg. The control group was administered from the tail vein with physiological saline (Otsuka Pharmaceutical Co., Ltd.) at a dose of 30 ml/kg. n was 3 for both groups. Observation period was 7 days, and body weight measurement, hematological tests (red blood cell, white blood cell, platelet), and hematobiological tests (GOT, GPT, urea nitrogen), and autopsy with naked eye were conducted.

(2) Results

The body weight increase, the hematological test values (red blood cell, white blood cell, platelet), and the hematobiological test values (GOT, GPT, urea nitrogen) of the group administered with the anti-mouse Fas ligand antibody #58-11 were not significantly different from those of the control group. In addition, no abnormalities were found in the group administered with the anti-mouse Fas ligand antibody #58-11 by the autopsy with naked eye.

Example 13.

Effects of the Anti-mouse Fas Ligand Antibody in Heart Ischemic Reperfusion Injury (1) Method Rat heart ischemic reperfusion model was produced by repeating the procedure of Example 2. Anti-mouse Fas ligand antibody #58-11 was diluted with physiological saline supplemented with 0.1% albumin, and administered to the rats from their right femoral vein at a dose of 1 mg/5 ml/kg immediately after the start of the reperfusion. The control group was administered with IgG antibody (Cappel) derived from normal hamster serum at a dose of 1 mg/5 ml/kg. The group administered with the anti-mouse Fas ligand antibody #58-11 consisted of 3 rats, and the control group consisted of 3 rats. The measurement of the non-ischemic, ischemic and necrotic regions of the sections and the plasma creatinine kinase (CPK) measurement were conducted by repeating the procedure of Example 2.

(2) Results

Figure 17:
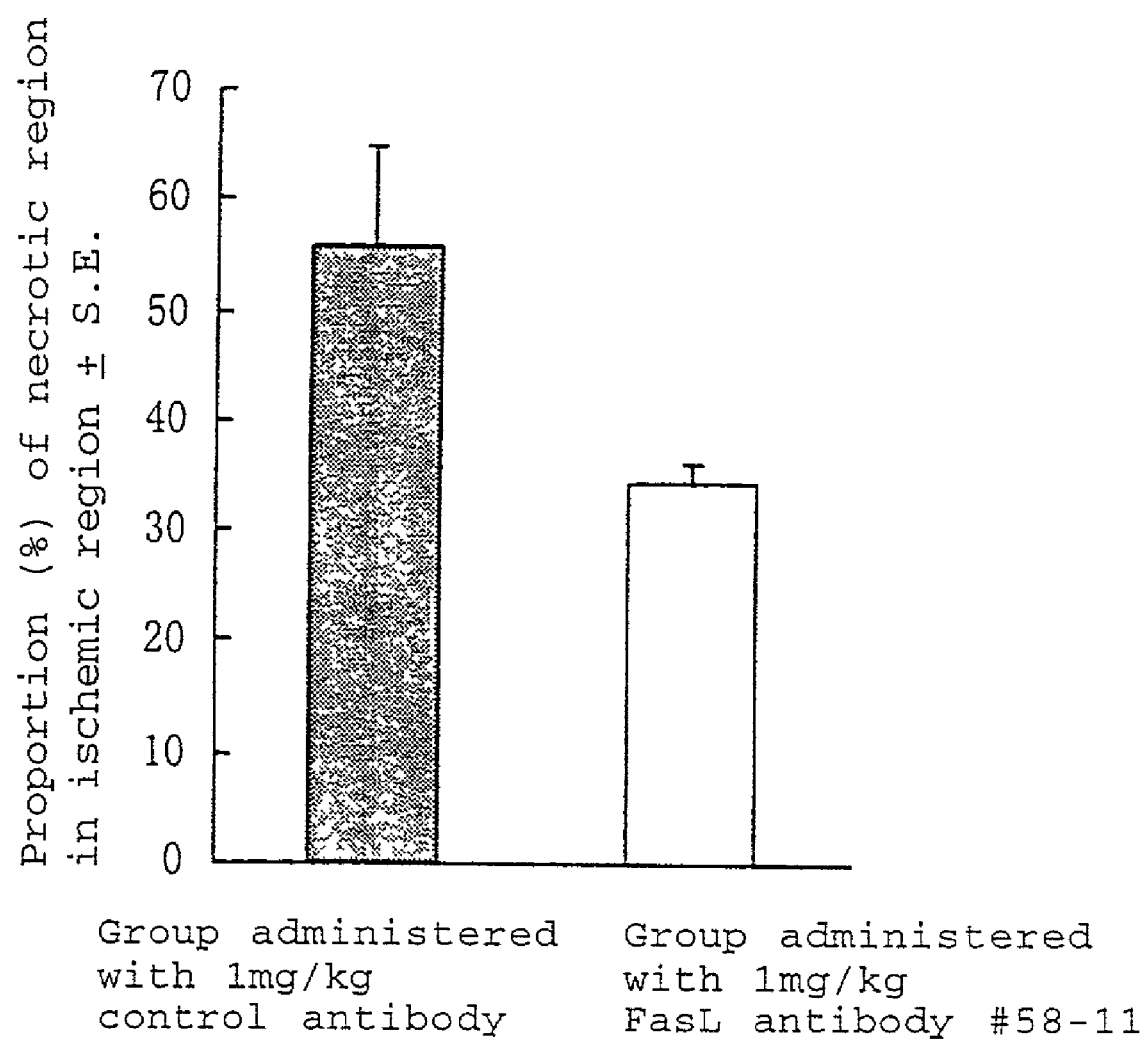
FIG. 17 is a view showing the suppressive effect of the anti-mouse Fas ligand antibody (#58-11) for myocardial infarction lesion in experimental rat model of heart ischemic reperfusion injury model.
Figure 18:
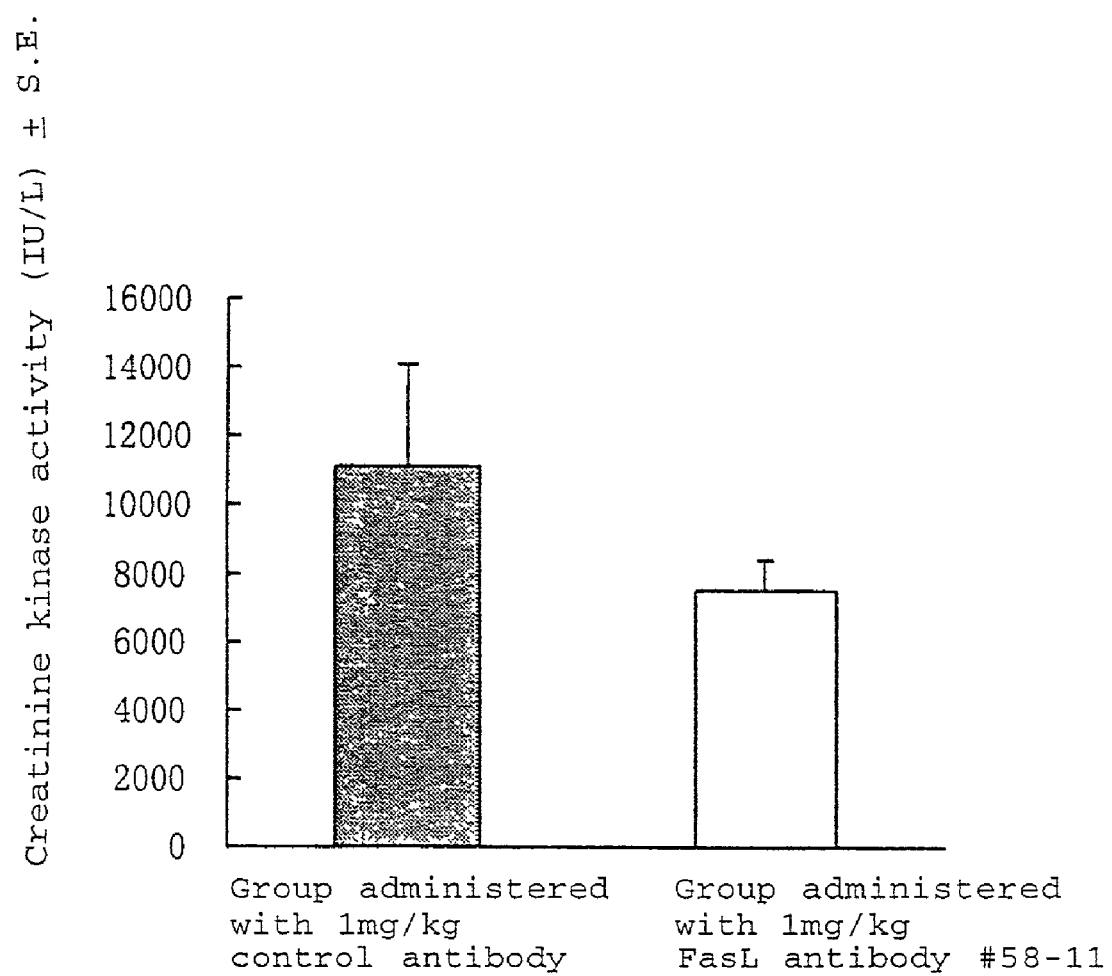
FIG. 18 is a view showing the suppressive effect of the anti-mouse Fas ligand antibody (#58-11) for increase of plasma CPK value at 3 hours after the reperfusion in an experimental rat model of heart ischemic reperfusion injury.

The proportion (%) of the necrotic region in the ischemic region of the group administered with the anti-mouse Fas ligand antibody #58-11 was less than that of the control group (FIG. 17). The plasma CPK value of the group administered with the anti-mouse Fas ligand antibody #58-11 was less than that of the control group (FIG. 18).

Example 14.

Effect of the Anti-mouse Fas Ligand Antibody on Survival Rate in Mouse GVHD Model (1) Myelosuppression in the Host Mouse Male, 6 week old DBA/2 mice (Charles River Japan K.K.) were used for the host mice. The host mice were intraperitoneally administered with 350 mg/kg of cyclophosphamide ((Shionogi & Co., Ltd., Endoxan) to induce myelosuppression.

(2) Preparation of the Splenic Lymphocytes from the Donor Mouse, and Transplantation the Splenic Lymphocytes to the Host Mouse A male B10.D2 mouse of 7 to 8 week old (Nihon SLC K.K.) was used for the donor mouse. Spleen from the donor mouse was disintegrated in Hank's solution (manufacture by Nissui Seiyaku K.K.) with forceps and centrifuged, and the thus obtained cells were suspended in 0.017M Tris-0.747% ammonium chloride solution for selective hemolysis of erythrocytes. The residual cells washed with Hank's solution were used as splenic lymphocytes from the donor mouse, and $3 \times 10^7$ cells/mouse were transplanted to the host mice from their tail vein on the next day of the cyclophosphamide administration as described above.

(3) Evaluation of the Effects of the Anti-mouse Fas Ligand Antibody #58-11

Figure 19:
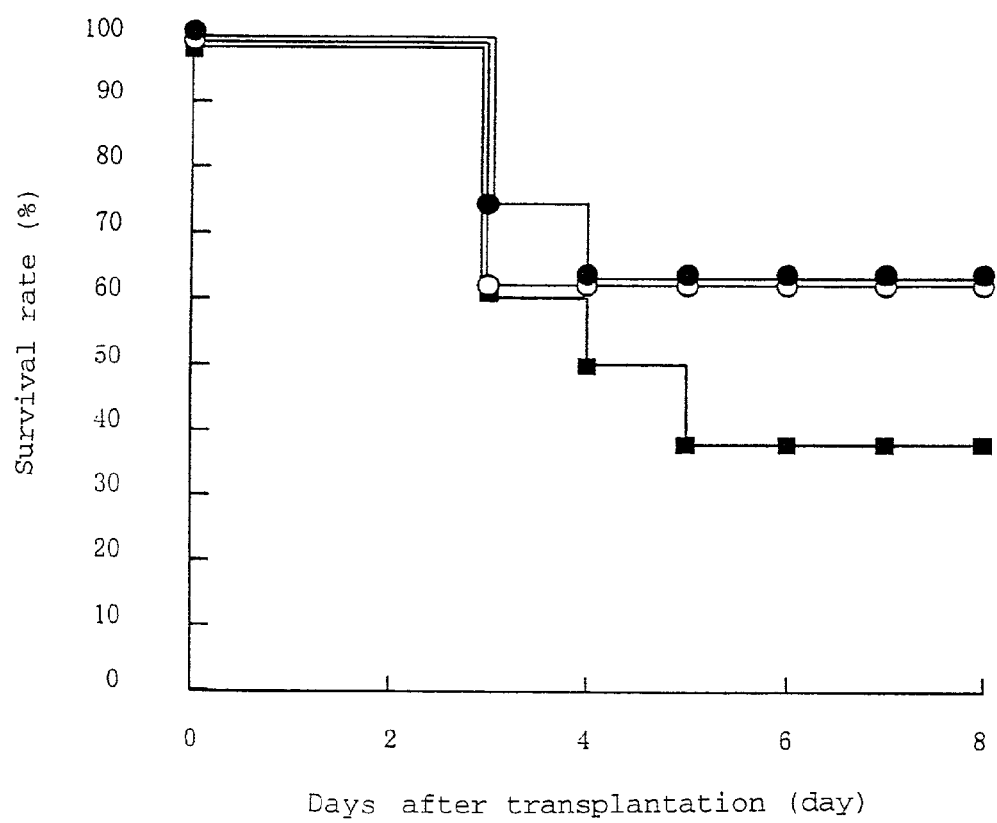
FIG. 19 is a view showing the effect of the anti-mouse Fas ligand antibody (#58-11) in improving the survival rate of mouse GVHD model. Blank circle (○) represents the survival rate of GVHD negative group, solid circle (●) represents the survival rate of the group administered with 10 mg/kg of #58-11, and solid square (■) represents the survival rate of the group administered with 10 mg/kg of the control antibody.

Survival rate was evaluated by administering 10 mg/kg of the anti-mouse Fas ligand antibody #58-11 or IgG antibody (Cappel) derived from normal hamster serum from the tail vein 30 minutes before the transplantation of the splenic lymphocytes from the donor mouse. It should be noted that, in the case of the GVHD negative group, the antibody was replaced with 10 ml/kg of physiological saline (Otsuka Pharmaceutical Co., Ltd.) which had been used for diluting the antibody, and the splenic lymphocytes were replaced with Hank's solution which had been used for suspending the lymphocytes (n was 8 for each group). The survival rate at 8th day after the transplantation of the splenocytes were 63% in the GVHD negative group, 63% in the group administered with the anti-mouse Fas ligand antibody #58-11, and 38% in the group administered with the control antibody. Comparison of the survival rate with the group administered with the control antibody revealed the survival rate-improving effect in GVHD for the group administered with the anti-mouse Fas ligand antibody #58-11 (FIG. 19).

Example 15.

Effects of the Anti-mouse Fas Ligand Antibody in Renal Ischemic Reperfusion Model (1) Production of Renal Ischemic Reperfusion Model Male, 6 week old ICR mice (Nihon SLC K.K.) were fixed in supine position on an operation plate after anesthetizing with pentobarbital, and abdominally dissected. Right kidney was extirpated from the abdominal opening, and ischemic condition was created by blocking the left renal artery and vein with a clip (VASCULAR CLIP AS-1, Kyowa Tokei Kogyo). After 30 minutes, the clip was undone and the blood was allowed to flow. Blood was collected from abdominal large vein 24 hours after the reperfusion, and measured for plasma creatinine and urea nitrogen. Creatinine was measured by using Detamina CRE 55s (Kyowa Medics), and urea nitrogen was measured by using Urea Nitrogen B TestWako (Wako Pure Chemical Industries, Ltd.) in an autoanalyzer (COBAS FARA, Roche)

(2) Administration of the Anti-mouse Fas Ligand Antibody #58-11

Anti-mouse Fas ligand antibody #58-11 was diluted with physiological saline supplemented with 0.1% BSA (SIGMA), and the mice were intravenously administered with the dilution at a dose of 0.3 mg/10 ml/kg or 3 mg/10 ml/kg immediately before the ischemia of the left renal artery and immediately after the reperfusion. The control group was administered with the physiological saline supplemented with 0.1% BSA. In the case of sham operated group, the physiological saline supplemented with 0.1% BSA was administered without creating the ischemic condition after the extirpation of the right kidney. All groups consisted of 8 cases.

(3) Results

Figure 20:
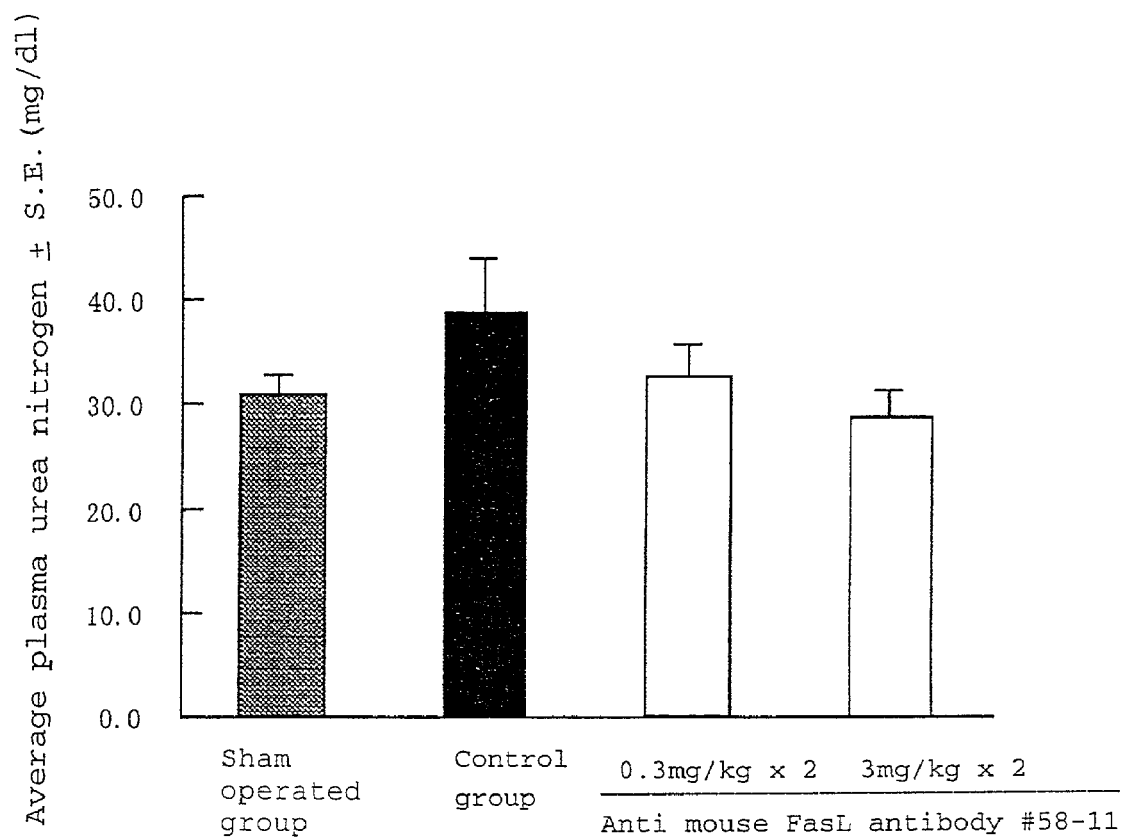
FIG. 20 is a view showing the suppressive effect of the anti-mouse Fas ligand antibody (#58-11) for increase of plasma urea nitrogen in a mouse renal ischemic reperfusion injury model.
Figure 21:
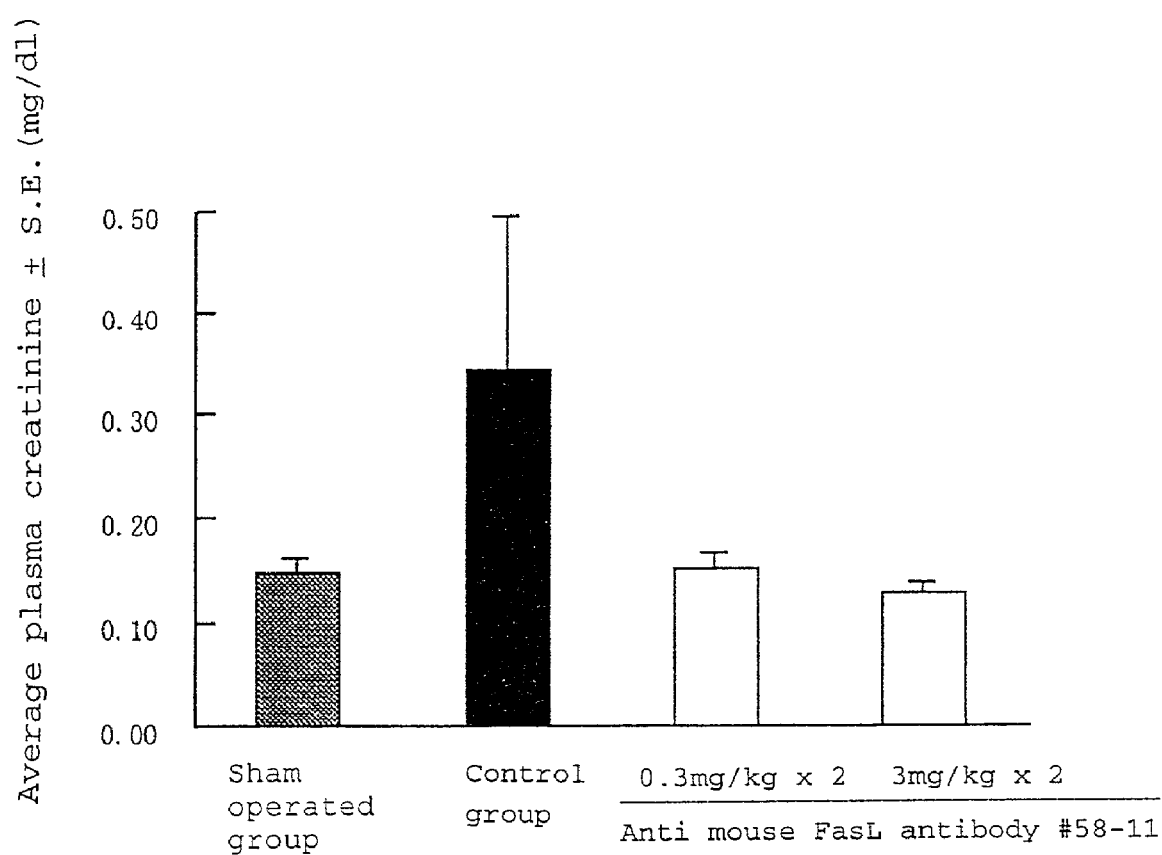
FIG. 21 is a view showing the suppressive effect of the anti-mouse Fas ligand antibody (#58-11) for increase of plasma creatinine in a mouse renal ischemic reperfusion injury model.

The plasma creatinine value and the urea nitrogen value of the group administered with 3 mg/kg of the anti-mouse Fas ligand antibody #58-11 were less than those of the control group to demonstrate the inhibitory effect for the renal ischemic reperfusion injury (FIGS. 20 and 21). The results as described above reveals that the prophylactic/therapeutic agent or the organ preservative agent of the present invention has excellent effects on various diseases. The prophylactic/therapeutic agent of the present invention exhibited no marked toxicity, and no toxicity was found at least in relation to the inhibition of biological actions of the Fas/Fas ligand system. Accordingly, the prophylactic/therapeutic agent of the present invention containing a Fas antagonist as its effective component is useful in treating the diseases wherein the biological action of the Fas/Fas ligand system, and in particular, the Fas-mediated cell death, and particularly, the apoptosis is involved so long as the signal generation or transduction by Fas is blocked and the biological action of the Fas/Fas ligand system is suppressed.

INDUSTRIAL UTILITY

The prophylactic/therapeutic agent of the present invention containing a Fas antagonist as its effective component suppresses the biological action of the Fas/Fas ligand system, and in particular, the Fas-mediated cell death, and particularly, the apoptosis, and exhibits prophylactic or therapeutic effects for various diseases. In addition, the prophylactic/therapeutic agent of the present invention has no marked toxicity, and no toxicity has been found at least in relation to the inhibition of biological actions of the Fas/Fas ligand system. Therefore, the Fas antagonist of the present invention should constitute a prophylactic/therapeutic agent for diseases wherein the cell death, and in particular, apoptosis is involved.

The invention claimed is:

1. A prophylactic or therapeutic method of treating graft versus host disease (GVHD) which comprises administering an effective amount of a Fas antagonist that interacts with the extracellular domain of the Fas ligand, to a patient in need thereof; wherein the Fas antagonist is an anti-Fas ligand antibody.

2. The method of claim 1, wherein said anti-Fas ligand antibody is a humanized anti-Fas ligand antibody.

3. A prophylactic or therapeutic method of treating graft versus host disease (GVHD) which comprises administering an effective amount of a Fas antagonist that interacts with the extracellular domain of the Fas ligand, to a patient in need thereof; wherein the Fas antagonist is a Fas extracellular domain or a derivative thereof.

* * * * *